United States Patent [19]

Sogi et al.

[11] 4,208,484
[45] Jun. 17, 1980

[54] APPARATUS FOR HANDLING CENTRIFUGE TUBES IN AUTOMATIC CULTURE SYSTEM

[75] Inventors: Shinroku Sogi; Makoto Yoshinaga, both of Hachioji; Toshio Shinohara, Chofu; Takayuki Aihara; Ikuo Tawara, both of Hachioji, all of Japan

[73] Assignee: Olympus Optical Co., Ltd., Tokyo, Japan

[21] Appl. No.: 885,599

[22] Filed: Mar. 13, 1978

[30] Foreign Application Priority Data

| Mar. 22, 1977 | [JP] | Japan | 52-30450 |
| Mar. 23, 1977 | [JP] | Japan | 52-34407[U] |
| Mar. 30, 1977 | [JP] | Japan | 52-37688[U] |
| Apr. 2, 1977 | [JP] | Japan | 52-40252[U] |
| Apr. 4, 1977 | [JP] | Japan | 52-40894[U] |
| Apr. 5, 1977 | [JP] | Japan | 52-38180 |
| Apr. 5, 1977 | [JP] | Japan | 52-38181 |
| Apr. 5, 1977 | [JP] | Japan | 52-41591[U] |
| Apr. 5, 1977 | [JP] | Japan | 52-41593[U] |

[51] Int. Cl.² ............................................. C12M 1/00
[52] U.S. Cl. ..................................... 435/286; 422/72; 435/284
[58] Field of Search ................... 195/127, 135; 233/26; 422/72; 435/287, 284, 286

[56] References Cited

U.S. PATENT DOCUMENTS

| 3,038,340 | 6/1962 | Isreeli | 73/423 |
| 3,151,073 | 9/1964 | Anthon | 233/26 X |
| 3,437,447 | 4/1969 | Harmon | 23/253 |
| 3,844,896 | 10/1974 | Sharpe | 195/139 |
| 3,953,172 | 4/1976 | Shapiro et al. | 422/72 |

Primary Examiner—Alvin E. Tanenholtz
Assistant Examiner—Robert J. Warden
Attorney, Agent, or Firm—Ostrolenk, Faber, Gerb & Soffen

[57] ABSTRACT

An apparatus for handling a centrifuge tube in an automatic culture system includes a centrifuge, above which is disposed a centrifuge tube carrying turntable which is intermittently driven through a given angular increment. Disposed at an equal spacing on and around the periphery of the turntable are centrifuge tube holder mechanisms each carrying a centrifuge tube holder. Also disposed in surrounding relationship with the turntable and at given positions where the latter comes to a stop are a plurality of processing stations including a centrifuge delivery unit which automatically delivers a centrifuge tube into the holder, a liquid disposal unit for disposing unnecessary culture solution from the centrifuge tube which has been subjected to the action of the centrifuge, a discharge unit for discharging a used centrifuge tube subsequent to the completion of the culturing operation, a transfer unit for transferring a centrifuge tube between the centrifuge holder mechanism and a holder receiver located within the centrifuge. As the turntable is incrementally driven, the centrifuge tube is successively conveyed through a culture treatment and a centrifuge tube processing position.

32 Claims, 31 Drawing Figures

FIG. 5
FIG. 6
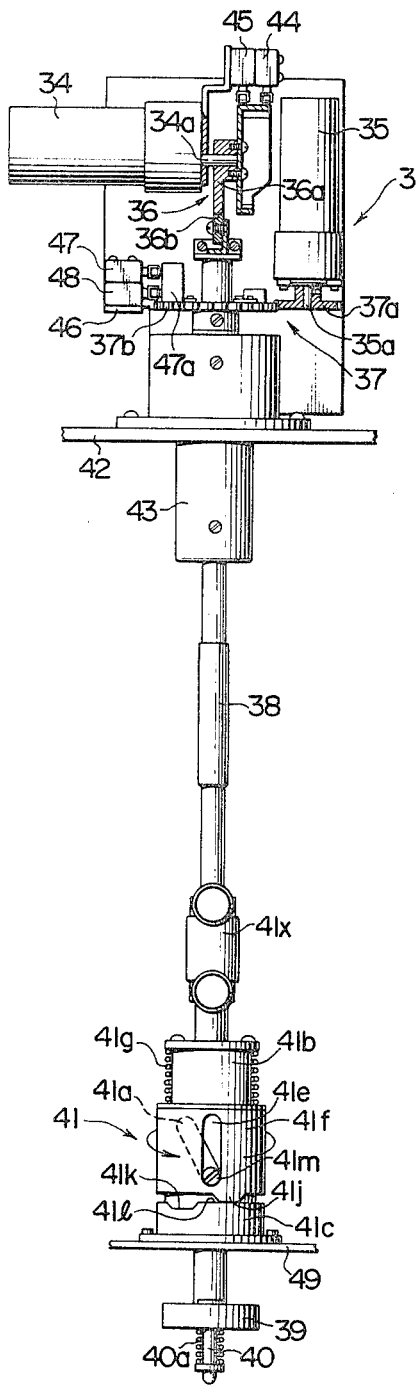
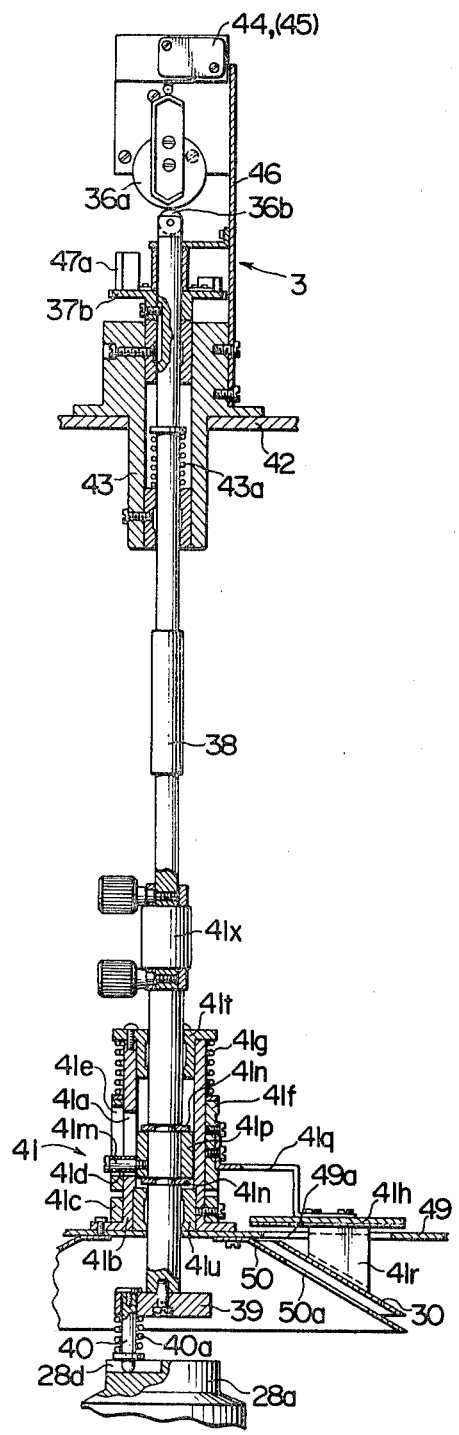

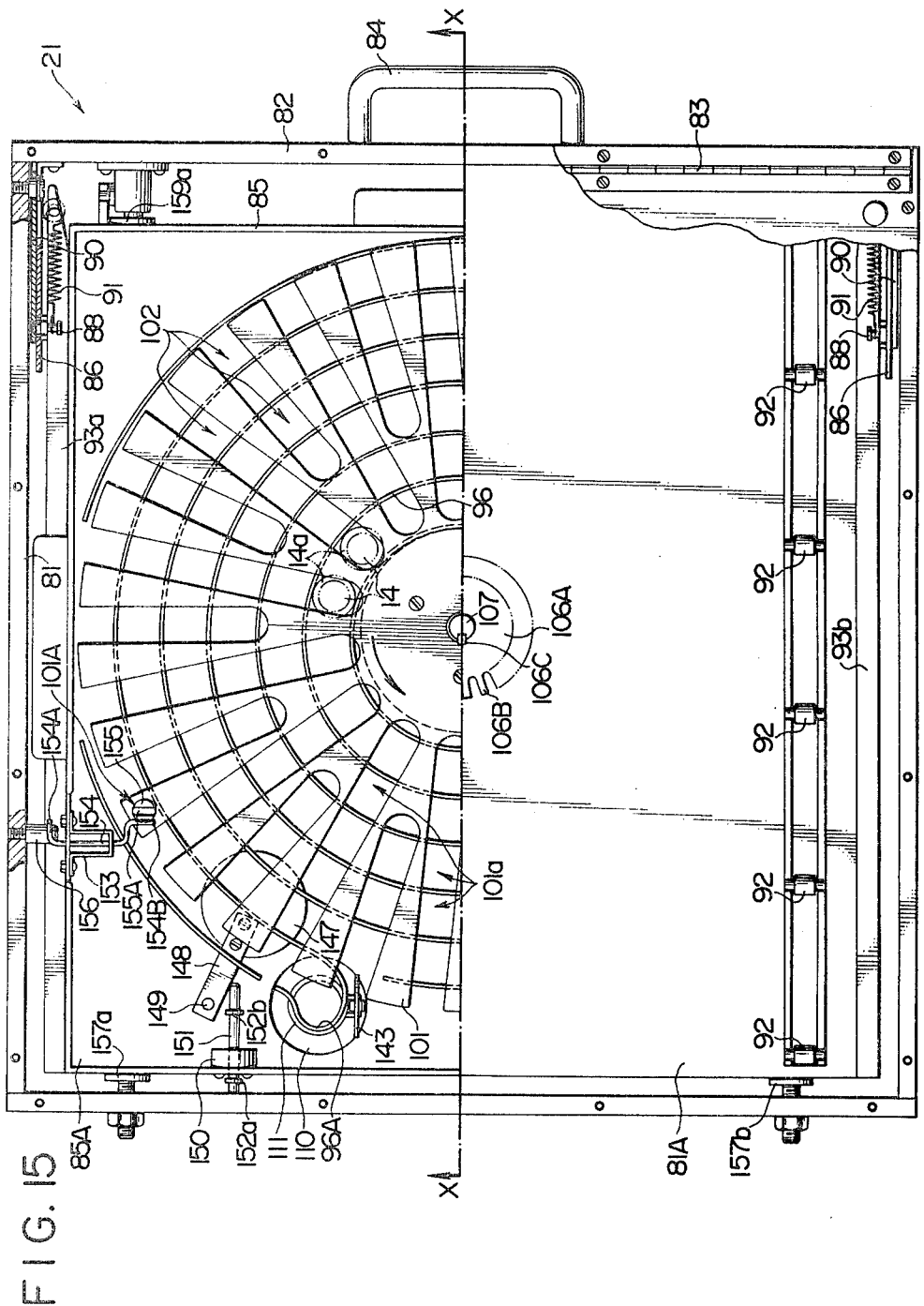

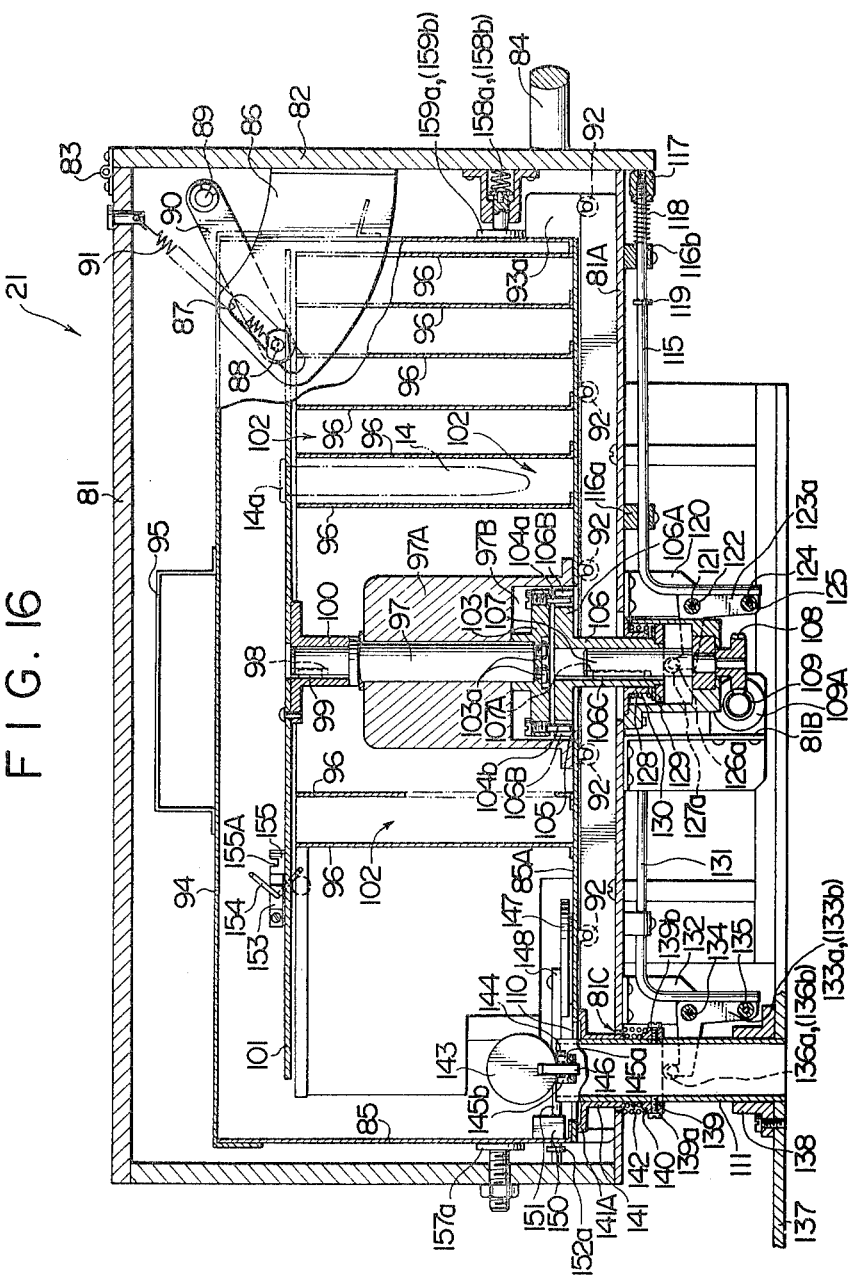

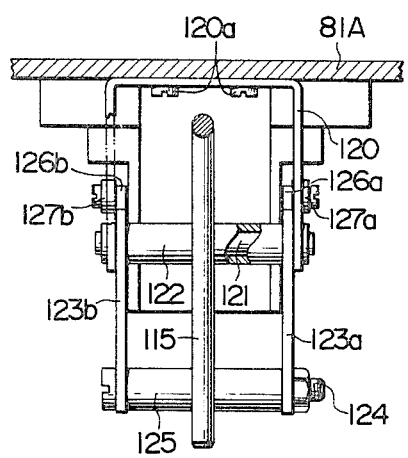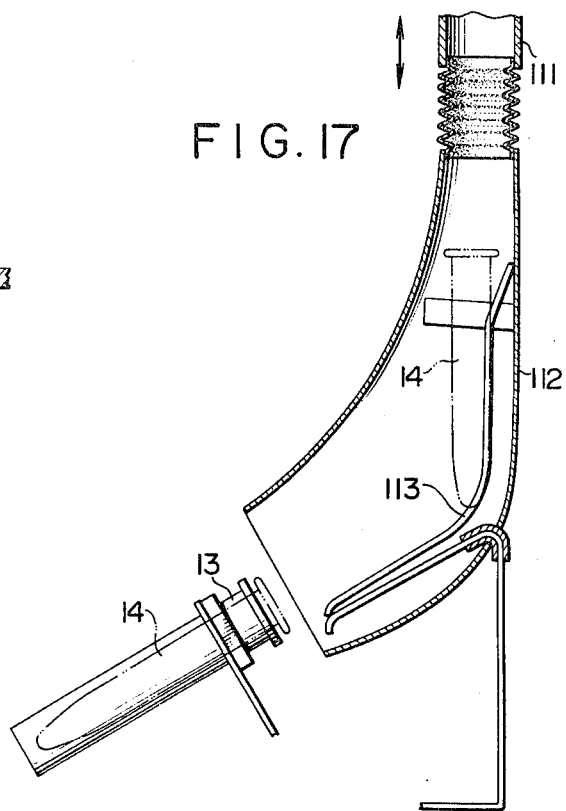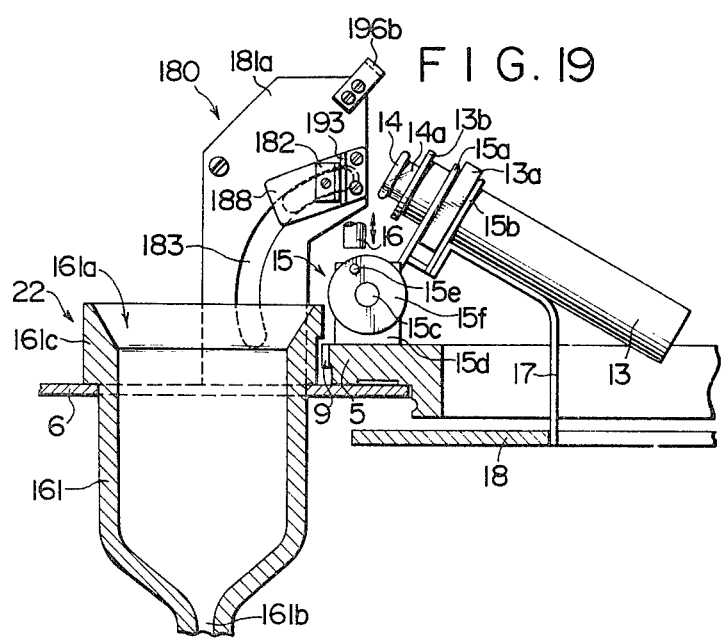

APPARATUS FOR HANDLING CENTRIFUGE TUBES IN AUTOMATIC CULTURE SYSTEM

BACKGROUND OF THE INVENTION

The invention relates to an apparatus for handling a centrifuge tube in an automatic culture system which achieves an automatic culturing of biological tissues such as cells.

As is generally recognized, the culturing of tissues such as cells takes place in a culture vessel a number of which are placed at still in a tissue culturing apparatus. In the conventional manual culturing operation of tissues, the culture vessel must be taken out of the apparatus and into the atmosphere in order to permit an observation of the results of culturing of tissues or to enable various operations which are necessary to perform a culturing over successive generations. The tissues are then moved out of a controlled environment such as a specific atmosphere, temperature and humidity maintained within the culture apparatus when it is moved into the atmosphere, and thus may be subject to a rapid change in the environment. In addition, the tissues may be contaminated by miscellaneous strains present in the atmosphere.

The present applicant has previously proposed a tissue culture apparatus which enables all of necessary culturing operations to be automatically performed under a given environment maintained in the interior thereof in order to overcome above difficulties. With this automatic culture apparatus, tissues which are to be cultured over successive generations are diluted with a culture solution and are injected into a culture vessel in suspension, and the vessel is placed at still under a specific environment maintained within the culture apparatus for purpose of culturing. After a given period of time, the vessel is conveyed to an observation position within the apparatus for inspection of the culturing result under a microscope. When it is confirmed that the tissue growth has increased to the full extent of the vessel, it is moved to a distribution position within the apparatus where a culturing solution is drawn with a pipette from the vessel and disposed. Subsequently, the tissue remaining in the vessel is rinsed by injection of a buffer solution, which is then drawn with the pipette and disposed. Subsequently, an enzyme solution such as tripsin is injected into the vessel and the latter allowed to stand still until the tissues which attached to the bottom surface of the vessel is almost free to be released therefrom. Thereafter, the enzyme solution is drawn with the pipette from the vessel and disposed, and a culture solution is again injected into the culture vessel. By repeatedly withdrawing and discharging the culture solution with the pipette, the solution is agitated to free the tissue completely from the bottom surface of the vessel, leaving it in suspension in the culture solution. The tissues in suspension are removed with the pipette and transferred into a centrifuge tube, which is subjected to the action of a centrifuge in order to achieve a separation between the culture solution and the tissues. Thereupon, the tissues having a greater specific gravity will attach to the bottom of the tube while the culture solution will be supernatant. The unnecessary culture solution is disposed by decantering the centrifuge tube. Subsequently, a culture solution is again injected into the tube, and is also agitated by the similar withdrawal and discharge operation mentioned above, using a pipette, so that the tissues are in uniform suspension in the culture solution contained within the tube. It is then distributed into a pair of fresh culture vessels in equal amounts, thus completing a single culturing operation. The culturing of tissues over successive generations requires a plurality of such culturing operations to be effected upon respective tissues contained in a number of culture vessels.

The centrifugation is required during the culturing operation because the enzyme solution which is injected into the vessel to render the tissues, which adhere to the bottom surface thereof, almost free cannot be completely withdrawn and disposed by the use of a pipette. A small amount of the enzyme solution may remain adhering to the bottom surface of the vessel or between the tissues. Under this condition, the tissues cannot be suspended in the fresh culture solution which is injected subsequently when they are distributed into the pair of fresh culture vessels. For this reason, the centrifugation is utilized while the tissues are in suspension in the previous culture solution in order to separate any remaining enzyme solution from the tissues. Also, part of the tissues which deceased in the process of culturing is also separated from the tissues which are to be used for the distribution.

To perform the various operations which are necessary to achieve the distribution from each of a number of culture dishes efficiently in the automatic culture apparatus described, it may be contemplated to provide a turntable on which a number of centrifuge tubes are mounted so that various operations can be performed at each angular position of the turntable. A centrifuge tube is mounted on the turntable at one angular position thereof, but must then be transferred to or from the rotor of a centrifuge, which constitutes a separate rotational system from the turntable. During the transfer, the rotor must be maintained stationary. However, the length of time during which the rotor is maintained stationary must be reduced as short as possible, since the total number of tissue specimens to be treated is almost doubled from generation to generation, so that toward the end of the culturing over successive generations, it will become necessary to operate the centrifuge almost continuously. Thus, the length of time during which the rotor must be maintained stationary represents a limitation on the number of generations over which the culturing can be continued.

The automatic culture apparatus described is provided with a distributor which is adapted to receive a pipette, falling in a vertical position, and which is rotatable to convey or transfer the pipette between a culture vessel and a centrifuge tube in various steps such as the withdrawal and disposal of the various solutions from the culture vessel, the transfer of the grown cells maintained in suspension in the culture solution into the centrifuge tube subsequent to the agitation of the solution in the vessel, and the distribution into a pair of fresh culture vessels of grown cells maintained in suspension in the centrifuge tube after the agitation thereof and the centrifugation. It is necessary that the pipette be replaced by a fresh one upon completion of each step mentioned above. Otherwise the solution of the previous step which adheres to the pipette may be admixed into liquid contained in a fresh culture vessel or centrifuge tube which is supplied to perform the next following step, thus exerting a significant adverse influence upon the culturing operation. For this reason, it is necessary to provide a very large number of sterilized pipettes during the operation of the automatic culture apparatus, and to feed them to the distributor or pipette supply station in synchronism with the operation of the apparatus.

For the same reasons, the centrifuge tube which is used for separation of the grown tissue or cells from unnecessary culture solution must be replaced for each specimen in order to prevent the contamination between successive specimens. As a consequence, a number of centrifuge tubes must be supplied to the automatic culture apparatus in order to permit a culturing of a number of tissue specimens. It is necessary to note that the centrifuge tube must be supplied one by one. A conventional apparatus employs a chain drive to feed the tube one by one. However, this arrangement does not lend itself to the culturing over successive generations since separate tubes must be supplied in continuous succession and since they cannot be readily sterilized.

The requirements for an arrangement which supplies a centrifuge tube to the automatic culture apparatus are given below.

1. The limited space allowance within an incubator which contains a variety of mechanisms and the number of centrifuge tubes required necessitate the capability to supply centrifuge tubes from the exterior of the incubator so that they can be additionally supplied whenever required.

2. The internal environment or atmosphere of the incubator must not be disturbed when externally supplying the centrifuge tube since a delicate control is involved.

3. Provision must be provided to facilitate the sterilization in order to prevent the penetration of the miscellaneous strains into the incubator.

4. Reliability of supplying centrifuge tubes one by one.

5. The operation and handling can be easily achieved.

As mentioned above, during the culturing process in the automatic culture apparatus, cells which have grown sufficiently within the vessel are injected into a centrifuge tube by using a pipette, and the tube subjected to centrifugation to separate the cells from the supernatant solution and deceased cells. Finally, the supernatant solution is disposed, and the empty centrifuge tube is disposed after completion of the distributing operation. The disposal of the centrifuge tube after its use is necessary because the cells cultured within the centrifuge tube are very susceptible to contamination by miscellaneous strains. Therefore, it is desirable that the centrifuge tube to which a supernatant solution from other cells being cultured may have attached be replaced by a sterilized centrifuge tube in order to minimize the attachment and growth of the miscellaneous strains and to assure the uniform quality of the tissues being cultured.

SUMMARY OF THE INVENTION

It is a first object of the invention to provide an apparatus for handling centrifuge tubes in an automatic culture system in which a turntable capable of carrying a plurality of centrifuge tubes on a common circle and at an equal spacing is disposed above a centrifuge and utilized to provide an efficient movement of the centrifuge tubes between a variety of handling positions so that the required handling or treatment can be automatically performed on the cells contained in the respective centrifuge tubes at each of the handling positions.

It is a second object of the invention to provide an apparatus for handling centrifuge tubes in an automatic culture system of the kind described above in which the transfer of a centrifuge tube between the turntable and the rotor of the centrifuge is performed by a transfer unit which accurately positions the rotor of the centrifuge and automatically opens an end cover of the centrifuge to permit an efficient transfer operation.

It is a third object of the invention to provide an apparatus for handling centrifuge tubes in which centrifuge tubes are detachably mounted on a turntable by using a centrifuge tube holder which holds the centrifuge tube in a detachable manner, the apparatus including a centrifuge tube holder mechanism mounted on the turntable which is capable of detachably and tiltably supporting the holder.

It is a fourth object of the invention to provide an apparatus for handling centrifuge tubes in an automatic culture system including a centrifuge tube delivery unit capable of any operation required for the supply of a centrifuge tube, the unit being located adjacent to a turntable at a given position thereof.

It is a fifth object of the invention to provide an apparatus for handling centrifuge tubes in an automatic culture system in which the disposal of unnecessary culture solution from a centrifuge tube subsequent to the centrifugation step is effected by a disposal unit located adjacent to the turntable at a disposal position thereof and which effects a tilting of the centrifuge tube and a holder therefor in conjunction with the operation of the holder mechanism to permit a complete disposal.

It is a sixth object of the invention to provide an apparatus for handling centrifuge tubes in an automatic culture system in which the disposal of unnecessary culture solution from the vessel subsequent to the automatic centrifugation is effected by a disposal unit by a tilting of a centrifuge tube and a holder therefor and in which means is provided to prevent a free fall of the centrifuge tube from the holder by its own gravity.

It is a seventh object of the invention to provide an apparatus for handling centrifuge tubes in an automatic culture apparatus in which the discharge of used empty centrifuge tubes from the turntable to the outside of the culturing environment is effected by a discharge unit located adjacent to the turntable at a discharge position thereof and which causes the holder to assume an inverted position to permit the centrifuge tube to be removed from the holder and externally lef while avoiding damage thereto.

In accordance with the invention, the entire operation of the automatic culture system from the transfer of a centrifuge tube to the centrifuge to the distribution of centrifuged tissues can be automatically achieved. In addition, the turntable undergoes a rotation within a limited space maintained in a given culturing environment. At each angular position of the turntable, a variety of handling or operating mechanisms operate upon centrifuge tubes either before or after centrifugation either simultaneously or sequentially, thus permitting a minimization of the size of the apparatus and an improved handling efficiency. Since the centrifuge tubes are regularly disposed on the turntable in respect to the operation of the centrifuge, the cells being cultured can be traced from the initial culturing vessel through the centrifuge tube to the distributed vessel, thus enabling the determination of the quality of lots by a sampling operation.

The arrangement of the turntable and the centrifuge one above another enables an accurate and automatic positioning of the rotor of centrifuge with respect to the turntable, thus contributing to an efficient transfer of a centrifuge tube therebetween and minimizing the time required therefor.

The end cover of the centrifuge is automatically opened in conjunction with the positioning of the rotor, thus dispensing with the provision of a separate end cover drive mechanism. When being opened, the end cover of the centrifuge undergoes rotation while being moved away from the mating part, thus avoiding the likelihood that miscellaneous strains or dust falls into the centrifuge to contaminate the cells.

The centrifuge tube is mounted in a holder when it is being conveyed. This avoids a damage to the centrifuge tube when it is transferred between the turntable and a receiver of the centrifuge and also when it is supplied or delivered to the turntable.

The centrifuge tube delivery unit of the invention is capable of containing a very large number of centrifuge tubes and feeding them one by one in a reliable manner. It may be disposed outside the incubator of the automatic culture system, thus preserving the limited space within the incubator and also avoiding the likelihood of communication between the incubator and the outer atmosphere through the delivery unit. The delivery unit includes an inner casing which can be replaced by another during the culturing operation in order to provide an additional supply of centrifuge tubes. The inner casing can be removed from an outer casing to facilitate the sterilization by a simple operation. When moving the inner casing into or out of the outer casing, as the closure of the outer casing is opened, a drive mechanism associated with a delivery rotary disc and a centrifuge tube guide pipe can be retracted to a level lower than the bottom plate of the inner casing, thus avoiding an interference therebetween. When the drive mechanism and the guide pipe are in their lower position, the interior of the inner casing is isolated from the outer atmosphere, and the guide pipe is closed by the lid, preventing the pentration of miscellaneous strains.

The liquid disposal unit of the invention achieves an automatic disposal of the solution by using a cam mechanism which causes a centrifuge tube to be tilted. This prevents the centrifuge tube to be excessively tilted. Also, subsequent to the centrifugation, an agitation of the cells, which may be experienced when disposing the supernatant liquid with a pipette, can be avoided, thus assuring a satisfactory disposal.

In accordance with the invention, means is provided for preventing a free fall of the centrifuge tube when it is automatically tilted by the operation of the holder mechanism. This means includes a resilient member which retains the centrifuge tube automatically, thus avoiding manual intervention. The resilient member contacts only the sidewall of the centrifuge tube and is maintained clear of the opening thereof, thus avoiding the penetration of the miscellaneous strains or dust through the opening.

The tube discharge unit of the invention includes a lid member or resilient plate which closes either one of the receiving opening of the centrifuge tube or the lower opening of a discharge pipe, thus preventing a direct communication between the inside and the outside of the culturing environment. In this manner, the cells being cultured can be effectively protected from miscellaneous strains or dust contained in the outer atmosphere. The resilient plate operates to absorbe part of the kinetic energy of the centrifuge tube as it falls down, thus preventing a damage thereto.

BRIEF DESCRIPTION OF THE DRAWINGS

FIG. 5 is a side elevation of a rotor positioning device for a centrifuge;

FIG. 6 is a cross section of an end cover operating device of the centrifuge;

FIG. 15 is a plan view of one form of a centrifuge tube delivery unit, with the upper half located above the line X—X being shown when the ceiling wall of the outer casing and the top cover of the inner casing are removed and the lower half being shown when the top ceiling of the outer casing and the inner casing removed to illustrate the interior of the outer casing;

FIG. 16 is a cross section of the delivery unit shown in FIG. 15;

FIG. 17 is a diagrammatic view of a feed path of a centrifuge tube as it is supplied from the delivery unit toward a holder on the turntable;

FIG. 18 is a side elevation of part of a mechanism for interlocking the delivery unit with the end cover of the outer casing;

FIG. 19 is a cross section of a liquid disposal unit;

DESCRIPTION OF PREFERRED EMBODIMENT

Figure 1:
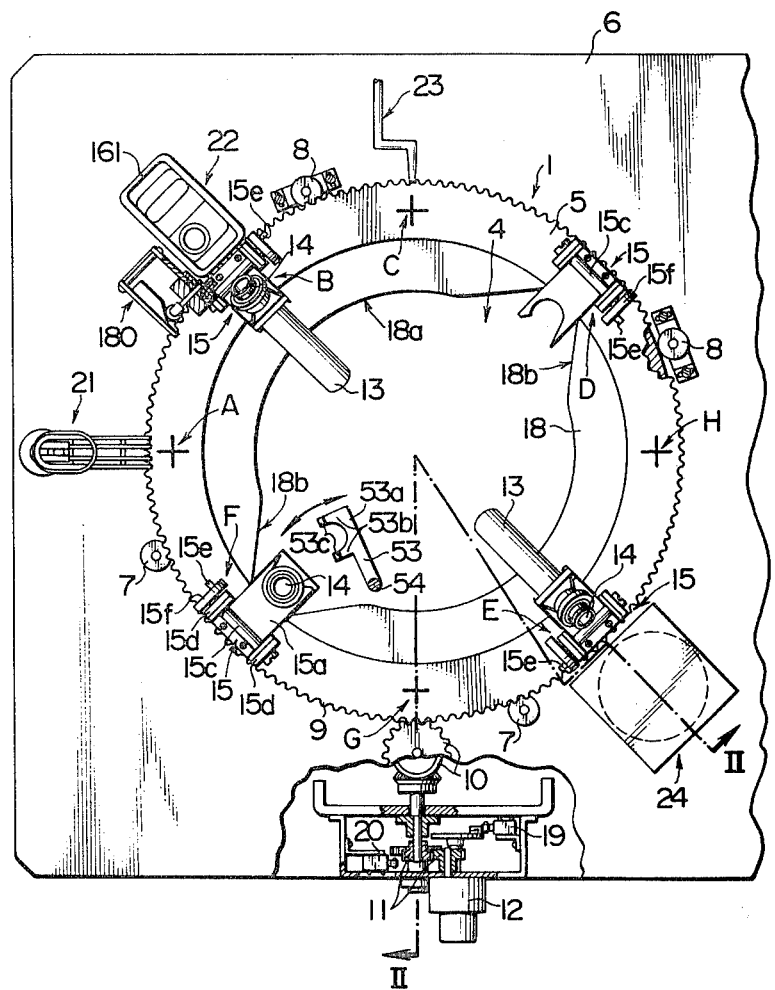
FIG. 1 is a schematic plan view of a centrifuge tube carrying turntable used in the apparatus of the invention.
Figure 2:
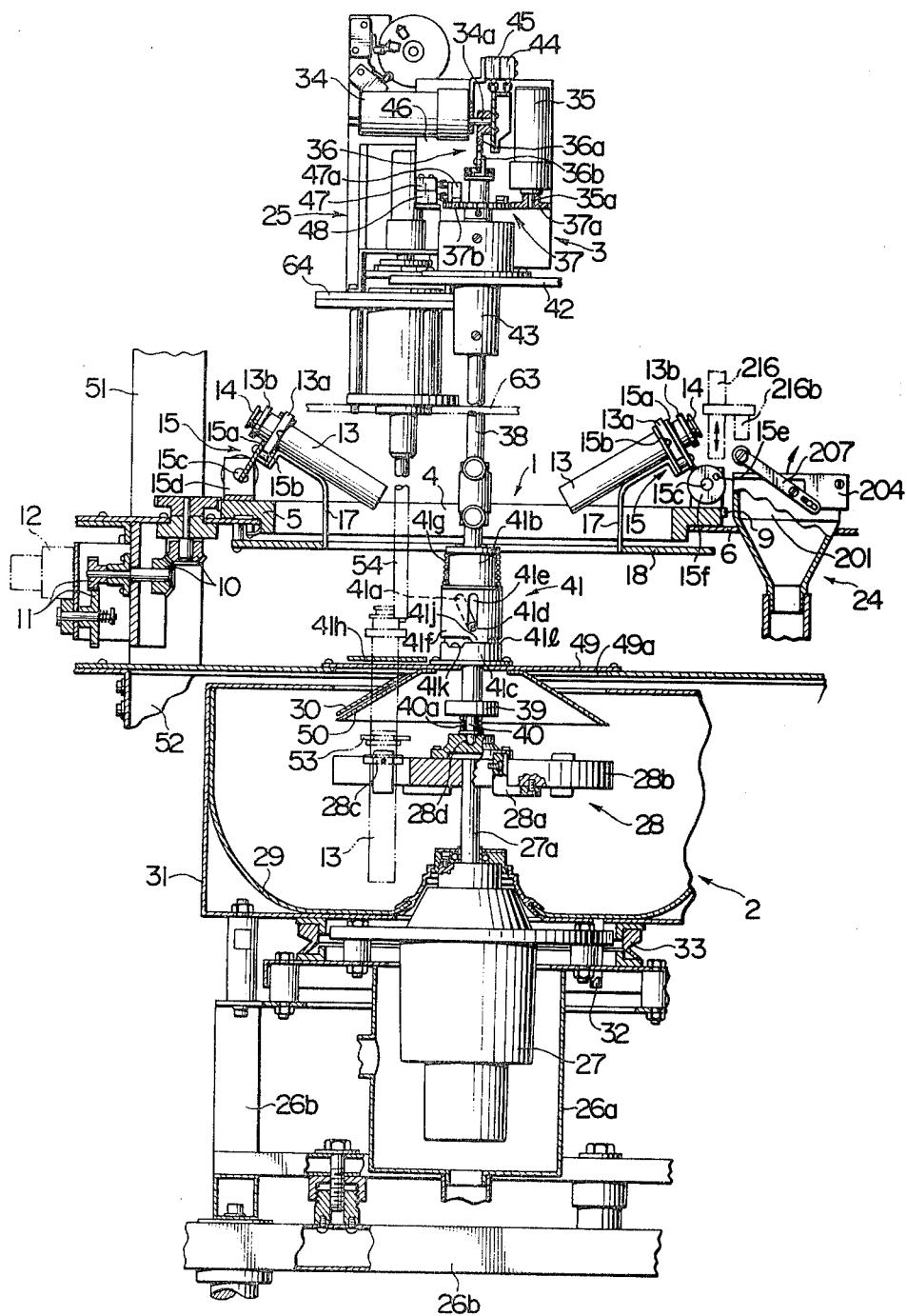
FIG. 2 is a side elevation, taken along the line II—II shown in FIG. 1, illustrating the interrelationship between various mechanisms.

Referring initially to FIGS. 1 and 2, there is provided a turntable 1 which is adapted to carry a plurality of centrifuge tubes. The turntable is rotatably mounted above a centrifuge 2 which is used for the centrifugation of cells being cultured from a culture solution contained in a centrifuge tube. The turntable is adapted to intermittently driven through a given angular increment about the axis of a rotor drive shaft 27a of the centrifuge 2. The turntable 1 is formed with a central opening 4 over which is located a drive mechanism 3 associated with a positioning shaft 38 (see FIG. 2) which opens an end cover 30 (FIG. 2) of the centrifuge 2 and positions the rotor 28 thereof when one of the centrifuge tubes is to be moved into or out of the centrifuge 2.

The turntable 1 comprises an annular rotary plate 5 in which the circular opening 4 is formed, a drive motor 12 connected with the rotary plate 5 for rotating it, a plurality of cam follower arms 17 which are connected with individual centrifuge tube holder mechanisms 15 located on the rotary plate 5 for tilting centrifuge tubes 14, and an annular cam disc 18 disposed at a fixed position below the rotary plate 5 and cooperating with the cam follower arms 17 to tilt the tubes 14 and to return them to an upright position.

The rotary plate 5 is rotatably fitted in an opening formed in a stationary plate 6, and is centered by a pair of stationary rollers 7 and another roller 8 which is displaceable radially of the plate 5. The rotary plate 5 is formed with an outer peripheral gear 9 which meshes with a pair of bevel gears 10 which are connected through a plurality of spur gears 11 with the drive motor 12 located outside the culturing environment.

The annular cam disc 18 is fixedly mounted on the stationary plate 5 at a position below the rotary plate 5, and has a central opening which is smaller than the central opening 4 formed in the rotary plate 5. The edge of this opening is formed as a cam profile 18a. A plurality of cam follower arms 17 engage the cam profile 18a to cause the centrifuge tube 14 carried by the centrifuge tube holder mechanism 15 to assume a tilted or an upright position as the plate 6 rotates. At opposite positions, the cam profile 18a includes a pair of recesses 18b which, when engaged by the follower arms 17, cause an angular movement of the holder mechanism to bring the centrifuge tube 14 carried thereby to its upright position. The centrifuge tube 14 assumes its upright position in its transfer position to the centrifuge 2, its supply and distribution positions. Each of the cam follower arms 17 is in the form of a folded strip which includes an obliquely upward extending portion which is connected with the holder mechanism and a vertically depending portion, the free end of which is adapted to bear against the cam profile 18a.

A pair of microswitches 19, 20 are disposed adjacent to the motor 12 to control the rotation of the rotary plate 5. These switches are appropriately operated during the rotation of the motor 12, and the signals therefrom are fed to a computer, not shown, which in turn produces an output signal to drive the motor 12 so as to cause an intermittent rotation of the rotary plate 5 through a given angular increment.

In the present embodiment, the rotary plate 5 and the opening 4 formed therein are both shown as circular in form, but it should be understood that they may assume any other configuration such as a square or rectangle, for example. Also, more than three centering rollers 7, 8 may be provided.

In one of stop positions of the turntable 1 which is shown in FIG. 1, a zone A on the upper surface thereof is located opposite to a centrifuge tube delivery unit 21, zone B to a liquid disposal unit 22 which is used to dispose a supernatant culturing solution, zone C to a culturing solution feeder or supply unit 23, zone D a distribution unit (not shown) and zone E to a centrifuge tube discharge unit 24. It is to be understood that a zone F represents a transfer position for transferring a centrifuge tube to or from the centrifuge 2.

The rotary plate 5 is provided with a plurality of centrifuge tube holder mechanisms 15, which are eight in number including the zones A to F and two other intermediate positions H and G located between the zones D and E and E and F, respectively. The holder mechanisms 15 are located on a same radius of the rotary plate 5 at an equal angular interval. For the sake of brevity, only four mechanisms 15 are shown in FIG. 1, but it is to be understood that additional holder mechanisms 15 are present between the holder mechanisms 15 shown.

Figure 3:
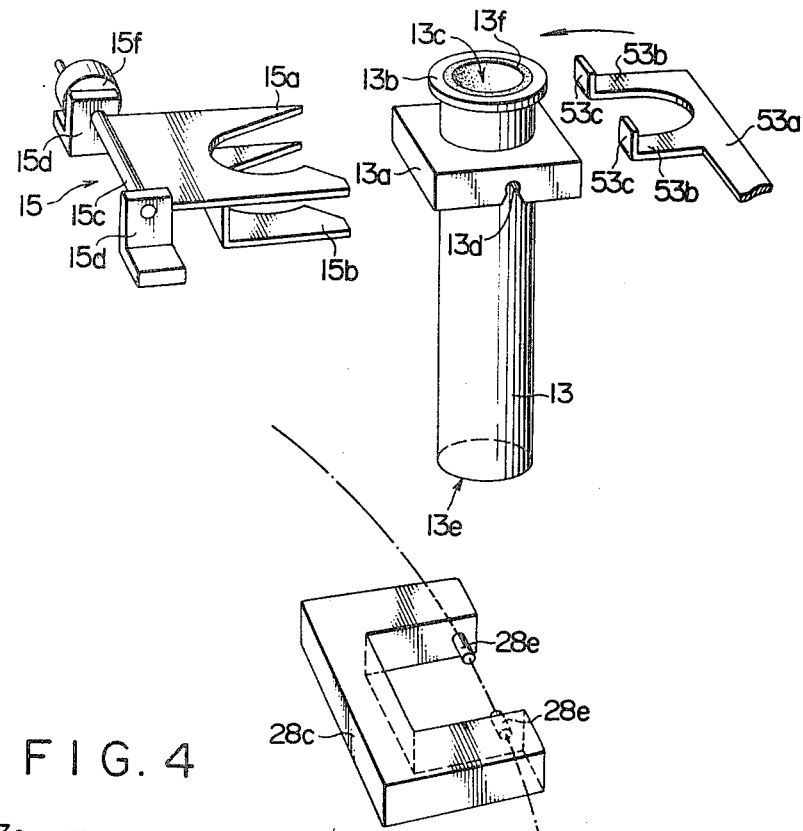
FIG. 3 is an exploded perspective view of a centrifuge tube holder mechanism.
Figure 4:
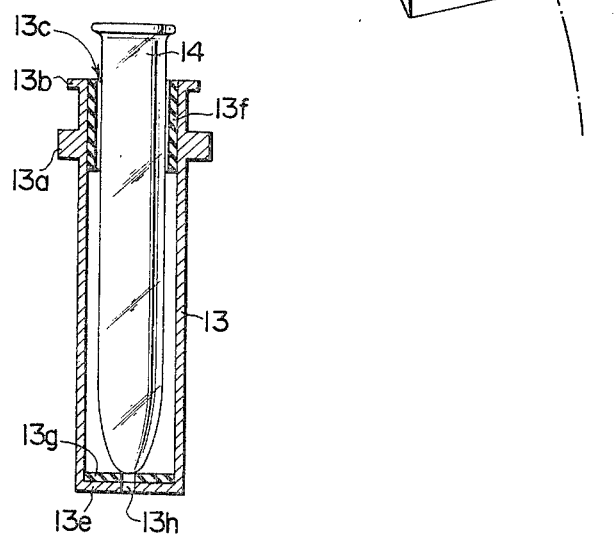
FIG. 4 is a cross section of a centrifuge holder.

FIG. 3 shows the construction of the holder mechanism 15 and a centrifuge tube holder 13 which is detachably held therein. The purpose of the mechanism 15 is to cause the holder 13 to assume a tilted or an inverted position whenever such position is required. The holder 13 is cylindrical in form and has an opening 13c in its top end for receiving a centrifuge tube. The top end is peripherally formed with an integral circular flange 13b, which is adapted to be engaged by grippers 53c of a carrier arm 53a on the transfer unit to be described later for transferring a centrifuge tube 14 to or receiving it from the centrifuge 2 at the transfer position. The cylinder which forms the holder 13 is peripherally provided with a rectangular flange 13a of a substantial thickness which is secured thereto at a position below the flange 13b. The flange 13a is adapted to be received between a pair of holder blades 15a, 15b of the mechanism 15. In this manner, the holder 13 can be detachably held by the mechanism 15. A pair of diametrically extending flutes 13d are formed in the lower surface of the flange 13a and are utilized to detachably mount the holder 13 on a rotor 28 of the centrifuge (see FIG. 2), by engaging with a pair of pins 28e extending toward each other from a channel-shaped holder receiver 28c mounted on the rotor 28. At this end, the flutes 13d has an increasing width in the downward direction to facilitate a positive engagement with the pins 28e. The holder is provided with a bottom wall 13e, and as shown in FIG. 4, the inner surface of the bottom wall 13e as well as the top portion of the inner wall of the holder 13 are lined with elastic members 13f, 13g, respectively, which may be formed of a silicone rubber sheet for cushioning purpose. The bottom wall 13e is centrally formed with a small hole 13h extending through the elastic member 13g to permit drops of water which may have condensed on the inner surface of the cylinder and on the outer surface of the centrifuge tube 14, received therein, to be drained to the exterior. The centrifuge tube 14 can be automatically inserted into the holder 13 by the delivery unit 11, and can be automatically removed therefrom by the discharge unit 24.

It is to be understood that the flange 13a need not be rectangular in configuration, but may be circular or polygonal. The location of the flange 13a is not critical, it being desirable that the centrifuge tube 14 can be held in a stable manner and can be sufficiently tilted during the centrifugation.

As shown in FIG. 3, the mechanism 15 comprises vertically spaced holder blades 15a, 15b which are formed with vertical aligned semi-circular notches to permit their abutment against the periphery of the holder 13. In addition, the mechanism includes a shaft 15c carrying the remote end of the blades 15a, 15b and rotatably mounted in a horizontal position on the turntable 1 by means of a pair of bearing members 15d, 15d. A rotatable disc 15f is mounted on one end of the shaft 15c which extends through one of the bearing members and carries an eccentric pin 15e (FIGS. 1, 2, 19 and 23) for rotating the shaft 15c. At the disposal and discharge zones B and E, the eccentric pin 15e is driven in a first direction by an elevating rod 16 or 216 (see FIGS. 2, 20 and 21) to rotate the shaft 15c about its own axis, thus tilting or inverting the holder 13. The shaft 15c is urged for rotation in a second, opposite direction by a return spring, not shown, extending between the shaft 15c and the bearing member 15d.

As shown in FIG. 2, the upper end of the cam follower arm 17 is secured to the lower blade 15b. Thus, when the cam follower arms 17 bear against the cam profile 18a, the holder 13 and the centrifuge tube 14 received therein can assume a tilted position in which it is directed toward the central opening of the annular cam disc 18 or an upright position.

Referring to FIG. 2, the centrifuge 2 comprises a drive motor 27 fixedly mounted, through its casing 26a, on a frame 26b outside the culturing environment. The rotor 28 of the centrifuge 2 is connected with an output shaft 27a of the motor and is capable of simultaneously centrifuging four centrifuge tubes 14. The rotor 28 includes a casing 29 having a top opening which is closed by an end cover 30. A housing 31 is fixedly mounted on the frame 26b and internally houses the rotor 28 and its casing 29.

The rotor 28 comprises a rotatable arm 28a which is connected with the upper end of the output shaft 27a and which is in turn connected with a rotating element 28b in which a receiver 28c for receiving the centrifuge tube holder is fixed. A single depression 28d is formed in the upper end face of the arm 28a and is removed from the axis of the shaft 27a. When the rotating element 28b remains at rest, the receiver 28c holds the holder 13 and the centrifuge tube 14 therein in vertical position shown in phantom line while it maintains the centrifuge tube 14 in a horizontal position by virtue of the centrifugal force during the rotation of the element 28b. The depression 28d cooperates with the drive mechanism 3 to determine the rest position of the element 28b when the centrifuge tube 14 is to be transferred.

A pipe 32 is provided to drain an amount of culturing solution which may have spilled into the casing 29 as well as drops of water to the outside of the centrifuge 2. A seal 33 is provided to protect the drive motor 27 against the culturing environment which maintains a humidity of 100%, thus enhancing the durability thereof.

A rotor positioning device determines the rest position of the rotor 28 so that the receiver 28c is aligned with the transfer unit to be described later. When the rotor 28 is located in this manner, the end cover 30 of the centrifuge is also opened. An end cover operating mechanism 41 and the drive mechanism 3 of the rotor positioning device are shown in FIGS. 2, 5 and 6. Specifically, the rotor positioning device comprises the positioning shaft 38 disposed above and in vertical alignment with the output shaft 27a, extending through the central opening 4 of the turntable 1. The shaft 38 is vertically movable and is also rotatable. The rotor positioning device also comprises a positioning pin 40 secured to the lower end of the shaft 38 in an eccentric manner therefrom. The positioning device also comprises the depression 28d formed in the upper end face of the rotor and engaged by the positioning pin 40, and the drive mechanism 3.

The vertical movement and the rotation of the positioning shaft 38 is controlled by the drive mechanism 3 which in turn includes a cam assembly 36 and a reduction gearing 37, driven by step motors 34 and 35, respectively. Intermediate its length, the shaft 38 is provided with the end cover operating mechanism 41.

The cam mechanism 36 comprises an eccentric disc cam 36a fixedly mounted on the output shaft 34a of the motor 34, and also comprises a cam follower 36a fixedly mounted on the upper end of the positioning shaft 38. The shaft 38 moves down through a given stroke when it is forced down by the cam 36a, and at the end of the downward stroke, it moves upward under the resilience of a return spring 43a (see FIG. 6) disposed within a shaft guide 43 which is secured to a stationary plate 42. The operation of the motor 34 is sensed by a pair of microswitches 44 and 45 which senses the home position of the cam 36a and the limit of rotation, respectively, and which feed the computer. However, it is to be understood that these microswitches may directly feed a suitable operating mechanism.

The reduction gearing 37 comprises a spur gear 37a fixedly mounted on the output shaft 35a of the motor 35 and which is in meshing engagement with another spur gear 37b fixedly mounted on the upper end of the positioning shaft 38, thus causing the latter to rotate about its axis. A microswitch 47 senses the home position and another microswitch 48 senses an angular position, the both switches 47, 48 being mounted on a support plate 46 and operated by a switch actuator 47a mounted on the spur gear 37b.

The positioning pin 40 which depends downwardly from a disc 39 extends therethrough, and is downwardly urged by a spring member 40a so as to be engageable with the depression 28d. The free end of the pin 40 is rounded, and when it does not engage the depression 28d, it moves across the upper surface of the rotatable arm 28a while bearing thereagainst. This maintains the pin 40 in its slightly raised position against the resilience of the spring 40a whenever the pin does not engage the depression 28d, and when it engages depression 28d, it moves downward to its lower limit. To the extent it engages the positioning pin 40, the depression 28d is preferably formed by a single, radially extending groove.

Figure 7:
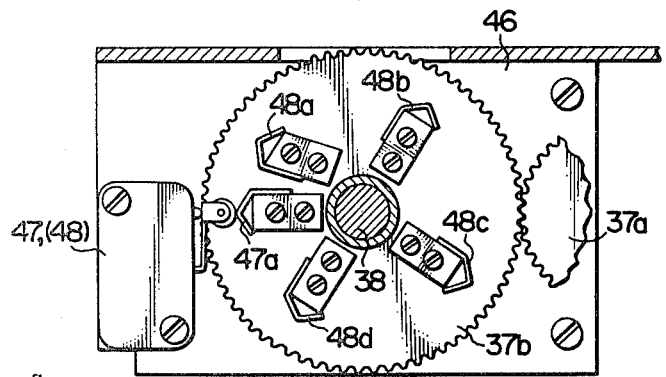
FIG. 7 is a plan view of a control mechanism which controls the positioning shaft of the positioning device shown in FIG. 5.

FIG. 7 is a plan view showing the switches 47, 48 and their relationship with respect to switch actuators 47a and 48a to 48d. In the example shown, the rotor 18 has the capacity to receive four centrifuge tubes at one time. For this reason, four actuators 48a to 48d are disposed at an equal angular spacing around the positioning shaft 38. These actuators 48a to 48d operate on the switch 48 in an appropriate manner. The actuator 47a is disposed on the spur gear 37b intermediate the actuators 48a and 48d.

In operation, the positioning shaft 38 is moved downward when the microswitch 47 is maintained in engagement with the actuator 47a. This causes the positioning pin 40 to move down also, but since the stop or rest position of the rotor 28 remains indeterminate, it cannot be expected that the downward movement of the pin 40 results in its engagement with the depression 28d. The motor 35 is then energized to rotate the spur gear 37b through 360° or until the actuator 47a again engages the switch 47. Thereupon, the free end of the pin 40 moves around the axis of the positioning shaft 48 while bearing against the upper end face of the rotatable arm 28a. Since the eccentricity of the pin 40 from the positioning shaft 38 is chosen equal to the eccentricity of the depression 28d from the output shaft 27a, there is one location during the rotation of the pin 40 where it engages the depression 28a as shown in FIGS. 2 and 6, thus bringing the rotor 28 to a given rest position. In this manner, it is assured that the position of the cells being cultured (centrifuge tube) before they are subjected to the centrifugation spaced from the position of the cells after being subjected to the centrifugation by a given angular interval, namely, the angular relationship between the switch actuators 48a to 48d and the switch 48. Hence, it is possible to load the cells at a particular position of the rotor 28 and to remove it to a given position on the turntable 1.

When the transfer of the cells is completed, the positioning shaft 38 is moved upward to disengage the pin 40 from the depression 28d. At the same time the end cover of the centrifuge 2 is closed, and the latter set in motion to effect the centrifugation of the cells from the culturing solution in the centrifuge tube received in the rotor 28.

The end cover operating mechanism 41 is constructed as shown in FIGS. 2, 5 and 6, and operates on a cover member 41h which covers and uncovers a fan-shaped opening 49a formed in a flat plate 49 secured above the housing 31 of the centrifuge 2, and also operates on the end cover 30 which covers or uncovers a fan-shaped opening 50a formed in an umbrella-shaped rotary cover 50. The mechanism 41 comprises a sleeve 41p which is rotatably fitted on the positioning shaft 38 for vertical movement together with the latter. A roller 41d is fixedly mounted on the sleeve 41p and projects radially outward therefrom. The roller 41d extends through a skewed slot 41a formed in a cylindrical, stationary guide member 41b through which the positioning shaft extends. The mechanism 41 also comprises a cylindrical member 41f which is rotatably fitted on the guide member 41b and which is formed with a longitudinal groove 41a engaged by the roller 41d, the cover members 41h, 30 being mounted on the cylindrical member 41f. Finally, the mechanism 41 comprises a fixed cam member 41c which causes a vertical movement of the cylindrical member 41f.

Referring to FIG. 6, the sleeve 41p is initially fitted on the positioning shaft 38 and is retained rotatable thereon by using a pair of snap rings 41n which engage mating peripheral grooves formed in the positioning shaft. The roller 41d is secured to the sleeve 41p by means of screw 41m in a manner such that the roller extends in the radial direction. The stationary guide member 41b is then secured to the plate 49 by using set screws, with the slot 41a receiving the roller 41d. The cam member 41c is mounted on the bottom of the guide member 41b, and the cylindrical member 41f is disposed above the cam member 41c. The cover member 41h is connected with the cylindrical member 41f by means of a bracket 41g, and the end cover 30 is connected also with the cover member 41h through another bracket 41r.

As viewed in FIGS. 2 and 5, the skewed slot 41a extends obliquely in the downward direction and to the right, and causes the cylindrical member 41f to rotate in a direction indicated by an arrow as the positioning shaft 38 moves down. The positioning shaft 38 is received in a pair of bearing members 41t, 41u, and a spring 41g urges the cylindrical member 41f downward or toward the fixed cam member 41c. The shaft 38 is formed in two parts, which are coupled together by a coupling 41x. In the example shown, the cam member 41c represents a face cam which is formed with a single recess 41k and a flat surface 41l (see FIG. 5), and the cylindrical member 41f is provided with a tab 41j of a configuration which corresponds to that of the recess 41k. It will be understood that the recess and the tab may be interchanged on the associated members.

When transferring the centrifuge tube 14 which contains cells being cultured between the turntable 1 and the centrifuge 2, the positioning shaft 38 is caused to move down by the step motor 34 which operates in response to a signal supplied from other operating mechanism. Thereupon, the sleeve 41p and roller 41d also move down. Since the downward movement of the roller 41d is guided by the skewed slot 41a in the stationary guide member 41b, the sleeve 41p and the roller 41d also rotate around the positioning shaft 38. At the same time, the cylindrical member 41f which has its groove 41e engaged by the roller 41d rotates in the same direction as the latter. Then, the tab 41j is disengaged from the recess 41k on the flat surface 41l of the cam member 41c, thus causing the cylindrical member 41f to rise by a corresponding amount vertically. This rising motion of the cylindrical member 41f moves the cover members 41h, 30 away from the surface of the plate 49 and the rotary cover 50, respectively. The continued rotation of the cylindrical member 41f opens the openings 49a, 50a. In this manner, it will be understood that the cover members 41h, 30 are maintained in contact with the surface of the plate 49 and rotary cover 50 as a result of the fitting engagement between the tab 41j and the recess 41k when they are closed while they are removed from such surface when they are to be opened. This prevents the ingress of miscellaneous strains and dust from falling into the centrifuge 2 during the normal operation, and also prevents such miscellaneous strains and dust which accumulate on the surface of the plate 49 and rotary cover 50 from being displaced when these cover members are to be opened.

When the transfer of the centrifuge tube is completed, the step motor 34 is energized again in response to a signal from other mechanism, causing the rotary cam 36a to rotate. The positioning shaft 38 is then raised under the resilience of the spring 43a. The mechanism 41 operates in the reverse manner from that mentioned above to close the openings 49a, 50a. In FIG. 2, numerals 51, 52 represent frames which are used to fixedly mount support plates 6, 42, 49, 46 in place.

Transfer Unit

The transfer unit is utilized during the time the turntable 1 remains stationary to transfer the centrifuge tube 14 located at zone F on the rotary plate 5 (see FIG. 1) toward and delivers it to the receiver 28c formed on the rotor 28 of the centrifuge 2 or to transfer the centrifuge tube mounted on the receiver 28c of the centrifuge toward and delivers it to the centrifuge tube holder mechanism located at zone F on the rotary plate 5.

Figure 8:
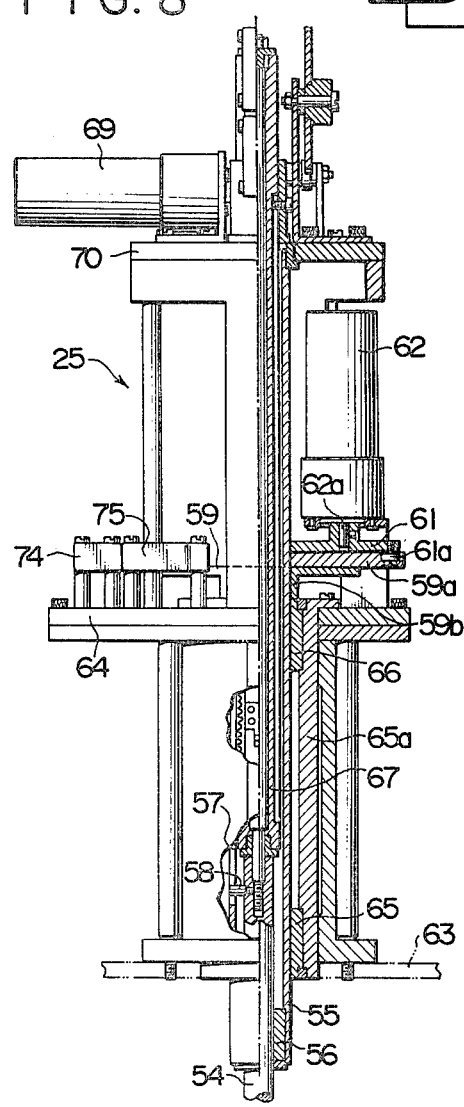
FIG. 8 is a side elevation, partly in vertical section, of a drive mechanism associated with an elevating shaft used in a centrifuge tube transfer unit.

Referring to FIGS. 2 and 8, the transfer unit comprises an elevating shaft 54 which extends downwardly through the central opening 4 and having a holder support member 53 mounted on its lower end which extends toward the rotor 28 of the centrifuge 2. The carrier arm 53a (FIG. 3) is fixedly mounted on the holder support member 53 and has grippers 53c which are engageable with the flange 13b of the holder 13. The transfer unit also comprises a rotary drive mechanism for the elevating shaft 54 which angularly displaces the grippers 53c between the centrifuge tube mounting and removal position F on the turntable and an intermediate position which is located directly above the rotor 28 of the centrifuge 2. Finally, the transfer unit comprises a vertical drive mechanism for the elevating shaft 54 which moves the grippers 53c between the intermediate position and the rotor. The combined rotary and vertical drive mechanism is shown at 25 in FIG. 2, and is located adjacent to the drive mechanism 3 mentioned above. Referring to FIG. 3 momentarily, it will be seen that the conveyor arm 53a is provided with a pair of laterally extending fork-shaped portions 53b, the free end of which is bent upward to form the grippers 53c.

The construction of the combined rotary and vertical drive mechanism 25 for the elevating shaft 54 is shown in FIG. 8. Specifically, the elevating shaft 54 extends through a pipe 55, the lower end of which fixedly carries a bearing 56 for the shaft 54. The pipe 55 is formed with a longitudinally extending flute 57 into which is fitted a pin 58 secured to the shaft 54, thus causing the shaft 54 to rotate integrally with the pipe while maintaining it displaceable in the axial direction. At the middle, the pipe 55 is integrally provided with a disc 59 carrying a projection 59a, which is maintained, by a spring 60 (see FIG. 10), in contact with a roller 61a fixedly mounted on another disc 61 of a reduced diameter, which is in turn fixedly mounted on the output shaft 62a of a reversible drive motor 62. A mounting base 63 is fixed to the frames 51, 52 (see FIG. 2), and a support pedestal 64 is fixedly mounted on the base 63, the motor 62 being mounted on the pedestal 64. The base 63 and the pedestal 64 receive a sleeve 65a which internally carries a pair of bearings 65, 66. The upper bearing 66 receives the boss 59b of the disc 59, thus axially positioning the pipe 55.

A sleeve-shaped rack member 67 is connected with the shaft 54 for integral movement in the axial direction while permitting its rotation. The rack member 67 meshes with a pinion 68 (see FIG. 9) at its top end where it is located outside the pipe 55. The pinion 68 is fixedly mounted on the output shaft of a reversible motor 69 which serves as the vertical drive. The motor 69 is mounted on a pedestal 70 which is fixedly mounted on the pedestal 64.

Figure 10:
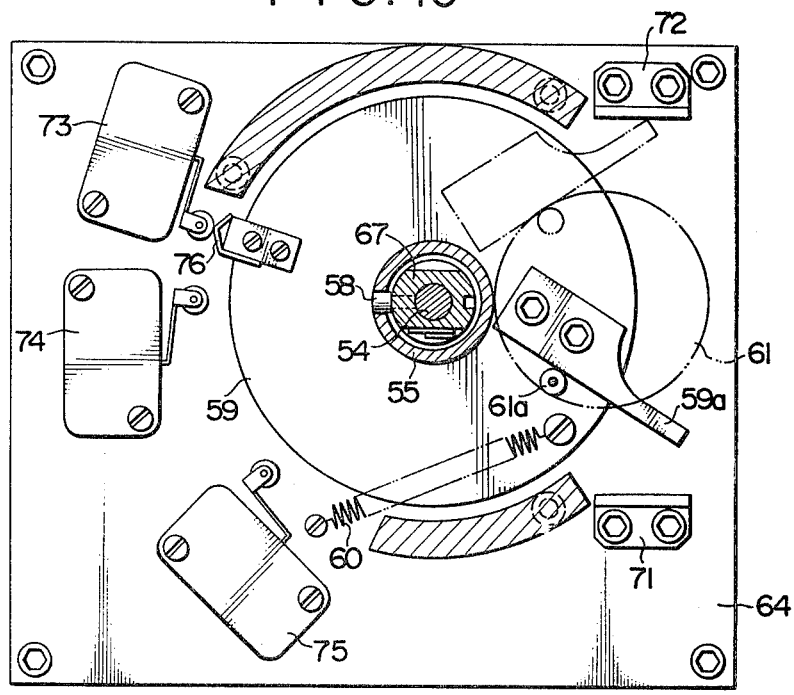
FIG. 10 is an enlarged top view of a rotary drive mechanism for the elevating shaft.

Referring to FIG. 10, the annular extent through which the shaft 54 can rotate is limited by a solid line and a phantom line position of the projection 59a. To assure that the disc 59 does not rotate beyond such limits, a pair of stops 71, 72 engageable with the projection 59a are disposed on the pedestal 64. Three microswitches 73 to 75 are disposed on the pedestal 64 and are operated by an actuator 76 secured to the disc 59 so that they are operated at a stop position, a first and a second angular position of the disc 59, respectively.

Figure 9:
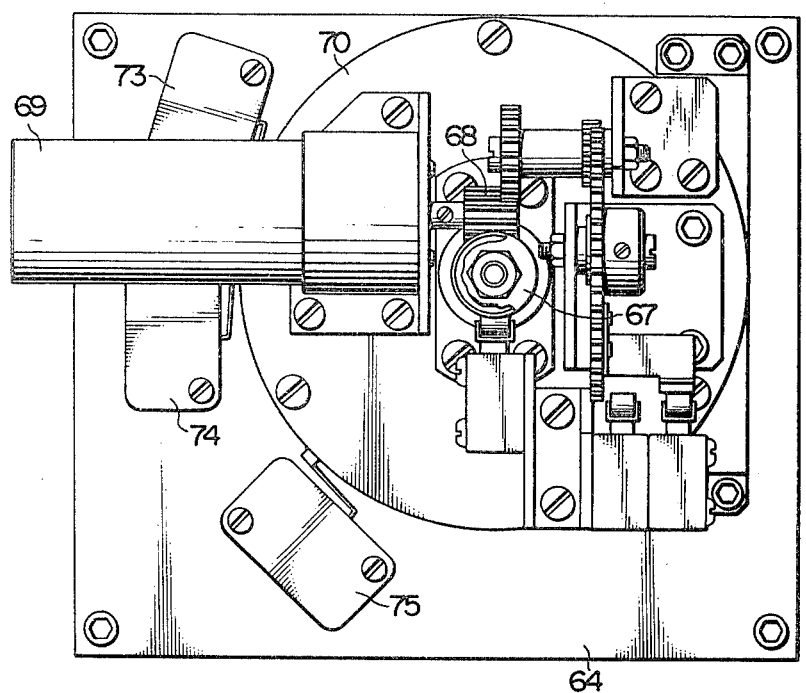
FIG. 9 is an enlarged top view of the drive mechanism shown in FIG. 8.

Referring to FIGS. 8 to 10, the manner in which the drive mechanism 25 rotates and vertically moves the grippers 53c and hence the centrifuge tube 14 engaging therewith will be described. Initially, the motor 62 is set in motion to rotate the centrifuge tube 14. The rotation of the motor 62 is transmitted to the disc 61 and the roller 61a. The roller 61a slides along the side of the projection 59a to move it angularly counter-clockwise from the solid line to the phantom line position shown in FIG. 10. When the motor 62 is driven in the opposite direction after the projection has reached the phantom line position, the projection 59a follows the movement of the roller 61a clockwise from the phantom line to the solid line position since it is urged against the roller 61a by the spring 60. The rotation of the projection 59a within such limited extent is transmitted to the holder support member 53 through disc 61, pipe 55, flute 57, pin 58 and shaft 54. During such transmission, there occurs a relative rotation between the shaft 54 and the rack member 67.

The centrifuge tube 14 can be vertically moved by energizing the motor 69 of the drive mechanism 25. The rotation of the motor 69 is transmitted to the pinion 68 to its meshing rock member 67. Since the shaft 54 moves integrally in the axial direction with the rack 67, the holder support member 53 can be moved vertically.

Figure 11:
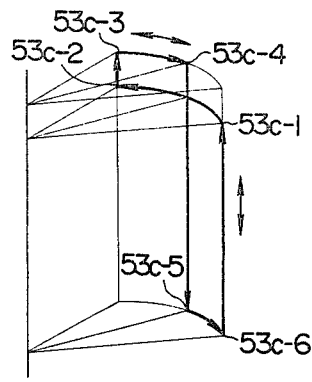
FIGS. 11 and 12A, B and C are diagrammatic views illustrating the operation of the transfer unit.
Figure 12A:
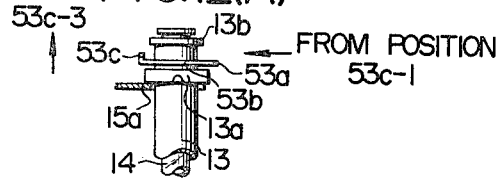
Figure 12B:
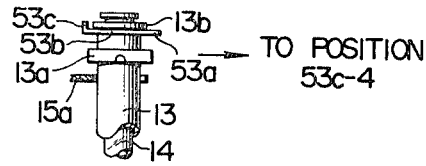
Figure 12C:
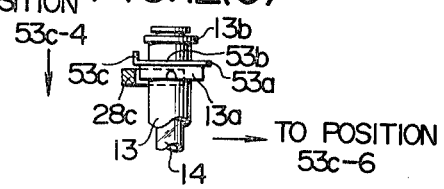

When transferring the centrifuge tube 14 from the turntable 1 to the centrifuge 2, the drive mechanism 25 may be controlled as described below. FIG. 11 is a diagrammatic view illustrating the movement of the grippers 53c which occurs as a result of the vertical and rotary movement of the elevating shaft 54 under the control of the drive mechanism 25. Assuming that the grippers (only one being considered) are in its initial position 53c-1, the rotation of the elevating shaft 54 brings it to position 53c-2 which is slightly below the flange 13b of the holder 13. The pair of fork-shaped portions 53b now engage the holder 13, as shown in FIG. 12A. When the elevating shaft 54 is then raised slightly, the grippers 53c move to an elevated position 53c-3, and the portions 53b and the grippers 53c bear against the flange 13b to push it up, thus maintaining the holder 13 and the centrifuge tube 14 received therein slightly raised from the holder balde 15a of the mechanism 15 (see FIG. 12B). Subsequently, the elevating shaft 54 is rotated in the opposite direction from the initial rotation to bring the holder 13 and the centrifuge tube 14 from the elevated position 54c-3 to an intermediate position 53c-4, located directly above the receiver 28c of the rotor 28, while holding them with the grippers 53c and the forks 53b. Now the elevating shaft 54 can be moved down until the grippers 53c reach a stop position 53c-5 immediately above the holder receiver 28c. Immediately before the stop position 53c-5 is reached, the flutes 13d formed in the lower surface of the flange 13a (see FIG. 3) are engaged by pins 28e on the receiver 28c, whereby the holder 13 and the centrifuge tube 14 are held by the receiver 18c. Then, the grippers 53c and the forks 53b move away from the flange 13b, and are located below this flange at the stop position 53c-5, as shown in FIG. 12C. Subsequently, the shaft 54 is rotated through a small stroke in the same direction as the rotation from the position 53c-3 to the position 53c-4. This brings the grippers 53c and the forks 53b to a position 53c-6 which is directly below the initial position 53c-1. At this position, the conveyor arm 53a clears the holder 13. Finally, the elevating shaft 54 may be moved upward to return the grippers 53c from the position 53c-6 to the initial position 53c-1. In this manner, the holder 13 and the centrifuge tube 14 disposed therein are automatically delivered or transferred to the receiver 28c of the centrifuge 2. It will be seen that the centrifuge tube 14 can be transferred from the centrifuge 2 to the turntable 1 by a procedure which is the reverse of what is mentioned above. The control of the direction in which the elevating shaft 54 is vertically moved or rotated by the drive mechanism 25 is achieved by switching the motors 69 and 62 between their forward and reverse rotations. A logic (not shown) including microswitches 73 to 75 controls the rotation at positions 53c-2, 53c-4 and 53c-6. A similar logic (not shown) controls the switching of the direction of vertical movement as well as the interruption thereof at positions 53c-1, 53c-3 and 53c-5. At this end, microswitches are disposed in relation to the motor 69.

Figure 13:
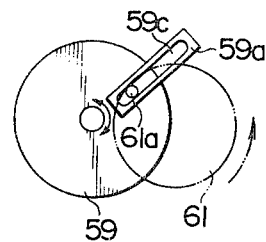
FIGS. 13 and 14 are plan views illustrating other examples of the rotary drive mechanism for the elevating shaft.
Figure 14:
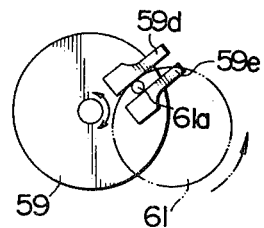

Rather than relying on the arrangement of FIG. 10 to control the angle through which the grippers 53c are rotated by the motor 62, such angle of rotation can be mechanically limited by an arrangement shown in FIG. 13. In this instance, the projection 59a is formed with an elongate guide slot 59c, in which the roller 61a is disposed. Alternatively, the disc 59 may be provided with a pair of opposing projections 59d, 59e, with the roller 61a interposed therebetween. In either instance, the rotation of the disc 59 in either direction is driven by the roller 61a, so that the spring 60 which has been used in FIG. 10 to return the disc 59 clockwise may be dispensed with.

Centrifuge tube delivery unit

As mentioned previously, the delivery unit 21 is disposed adjacent to the turntable 1 so as to correspond to zone A of rotary plate 5 to delivery a centrifuge tube automatically into the holder 13 maintained in the holder mechanism 15 which is located at zone A when the turntable 1 remains stationary.

Referring to FIGS. 15 and 16, the delivery unit 21 comprises an outer casing 81 having a closure 82 which is pivotally mounted at 83. An inner casing 85 may be placed within the casing 81 along the bottom thereof when the closure is opened. The casing 85 is internally provided with a guide wall 96 which defines a spiral guideway. The delivery unit 21 also comprises a rotary disc 101 which is disposed on top of the guide wall 96 and is rotatable about the center of vortex defined by the spiral guideway. The disc is formed with a plurality of radially extending delivery slots 101a, which define together with the spiral guide wall 96 a number of compartments, each of which is adapted to receive a single centrifuge tube 14. A guide tube 111 is provided to direct one centrifuge tube, which is located at the end of the spiral path and outside the region of the disc 101, toward the centrifuge tube holder as the disc 101 rotates.

Both casings 81 and 85 are box-shaped in configuration, and the closure 82 is provided with a handle 84 to facilitate its operation. As will be seen in FIG. 16, the closure 82 fixedly carries a pair of arms 86 adjacent to its opposite sides, the free end of these arms being formed with a slot 87 slidably receiving a pin 88 which is secured to the free end of a rockable arm 90 pivotally mounted at 89 on the sidewall of the outer casing 81. A tension spring 91 extends between the pin 88 and the ceiling wall of the casing 81. This arrangement permits the closure 82 to be maintained open.

To facilitate the loading and removal of the inner casing 85 into or from the outer casing 81, a plurality of rollers 92 are provided on the bottom wall of the casing 81 to permit the casing 85 to be slipped thereon. In addition, a pair of guide plates 93a, 93b (see FIG. 15) are provided adjacent to the opposite sides. As shown in FIG. 16, a shaft 97 is rotatably mounted in a bearing 97A at the central position of the spiral guideway 102 defined by the guide wall 96. In its top region, the shaft 97 is formed with an axial keyway 98, which is slidably engaged by a key 99 which is formed on the inside of a sleeve 100 fitted over the top end of the shaft 97. The sleeve 100 has an upper flange to which the rotary disc 101 is fixedly connected. As a consequence, when the shaft 97 rotates, the disc 101 also rotates. However, the disc 101 can be removed from the shaft 97. When the centrifuge tubes 14 are received in the spaces defined by the guideway 102 and the delivery slots 101a, they are held in suspension by the engagement between the upper flange 14a extending around the top opening of the tubes 14 and the upper surface of the disc 101. In this manner, the casing 85 houses more than one hundred centrifuge tubes 14 as a spiral succession.

A rotary drive mechanism is associated with the lower end of the shaft 97, as shown in FIG. 16. A recess 97B is formed in the lower surface of the bearing 97A and receives a disc 103 which is secured to the shaft by set screws 103a. A plurality of pins 104a, 104b depend downwardly from the disc 103 adjacent to the periphery thereof and extend into spaces between teeth 106B formed around the periphery of the flange 106A of a sleeve 106, the latter being moved upwardly through an opening 105 formed in the bottom plate 85A of the inner casing 85 when the casing 85 containing the centrifuge tubes 14 are loaded and the closure 82 closed. A shaft 107 slidably extends through the sleeve 106 in the axial direction thereof. A key 106C is formed on the inner wall of the sleeve 106, and engages a keyway 107A formed in the shaft 107, thus permitting an integral rotation of the shaft 107 and the sleeve 106. A worm gear 108 is fixedly mounted on the lower end of the shaft 107 and meshes with a worm 109 which is in turn connected with a motor 109A that is fixedly mounted on the bottom plate 81A of the outer casing 81 by means of bracket 81B. Thus it will be seen that when the motor 109A is set in motion under the condition that the pins 104a, 104b engage between the teeth 106B, the disc 101 is driven for rotation through the transmission comprising worm 109, gear 108, shaft 107, keyway 107A, key 106C, sleeve 106, teeth 106B, pins 104a, 104b, disc 103, shaft 97, keyway 98, key 99 and sleeve 100.

When the disc 101 is rotated counter-clockwise as shown by an arrow in FIG. 15, all of the centrifuge tubes 14 which are received in the compartments defined by the slots 101a and the guideway 102 move angularly along the guide wall 96 and are simultaneously displaced radially outward. At this time, the outermost centrifuge tube that is located at the end of the spiral succession of centrifuge tubes will be displaced away from the disc 101 to abut against a terminal guide wall 96A. An opening 110 is formed in the bottom plate 85A in alignment with the guide wall 96A, and hence upon abutting against the wall 96A, the centrifuge tube will fall down by gravity. As shown in FIG. 16, a centrifuge tube guide tube 111 extends into the opening 110 from below the outer casing 81 and is vertically movable. Consequently, the falling centrifuge tube will be received by the guide tube 111 and supplied to the holder 13 which is located outside. As shown in FIG. 17, the lower end of the tube 111 is connected with a conveyor tube 112 in which a pair of wire rails 113 are disposed to introduce the centrifuge tube into the centrifuge tube holder 13 which is disposed at an inclined position.

As mentioned above, when the inner casing 85 is disposed within the outer casing 81 and the closure 82 closed, the flange 106A on the sleeve 106 moves upward through the opening 105. A transmission mechanism which effects such movement will now be described. Referring to FIG. 16, an L-shaped rod 115 is disposed to be slidable along the bottom surface 81A of the outer casing 81. At the end of the horizontal portion, the rod 115 fixedly carries a head 117, and a compression spring 118 is disposed thereon between the head 117 and a guide member 116b, thus urging the rod 115 to the right, as viewed in FIG. 16. A stop ring 119 is fixedly mounted on the rod 115 to the left of the guide member 116b, and abuts against the guide member 116b when the closure 82 is freely opened, thus preventing an excessive movement of the rod 115 to the right. The vertical portion of the rod 115 extends inside a bearing plate 120, as shown in FIG. 18. The bearing plate 120 is channel-shaped in section and is secured to the bottom plate 81A of the casing 81 by set screws 120a. A shaft 121 extends between and supported by the both limbs of the bearing plate 120, and rotatably carries a sleeve 122 to which a pair of levers 123a, 123b of an inverted L-shape are fixedly mounted. Another shaft 124 extends between the other end of these levers 123a, 123b. A sleeve 125 is fitted on the shaft 124. The levers 123a, 123b have a horizontally extending portion, the free end of which is formed with an upturned end portion 126a, 126b (see FIG. 16) which in turn rotatably carries rollers 127a, 127b.

As shown in FIG. 16, a bearing 128 is fixedly mounted on the bottom plate 81A of the outer casing 81 for slidably receiving the sleeve 106. A flange 129 is secured to the lower end of the sleeve 106, and a compression spring 130 is disposed between the flange 129 and the bearing 128 for normally urging the sleeve 106 in the downward direction. The rollers 127a, 127b mounted on the projections 126a, 126b of the levers 123a, 123b bear against the lower surface of the flange 129. In the completely closed condition of the closure 82 as shown in FIG. 16, the rod 115 is driven to the left against the resilience of the spring 118. The free end of the vertical portion of the rod 115 urges the sleeve 125 to the left, whereby the levers 123a, 123b rotate clockwise about the shaft 121, causing the rollers 127a, 127b to push up the flange 129 against the resilience of the spring 130, moving the flange 106a of the sleeve 106 upwardly into the recess 97B in the bearing 97A through the opening 105 formed in the bottom plate 85A of the inner casing 85. As a consequence, the pins 104a, 104b engage between the teeth 106B of the flange 106A. On the other hand, when the closure 82 is opened, the rod 115 moves to the right, whereby the sleeve 106 is caused to move down under the resilience of the spring 130, retracting the flange 106A out of the inner casing 85. Under this condition, the flange 106A presents no interference with a movement of the inner casing 85 out of or into the outer casing 81.

An elevating mechanism for the centrifuge tube guide tube 111 will now be described. Referring to FIG. 16, it will be noted that there is provided a rod 131 which moves along the bottom plate 81A of the outer casing as the closure 82 is opened and closed, generally in the similar manner as the rod 115. An opening 81C is formed in the bottom plate 81A for passing the guide tube therethrough, and a channel-shaped bearing plate 132 is fixedly mounted adjacent to the opening and a pair of levers 133a, 133b which are identical in construction with the levers 123a, 123b are rotatably mounted on a shaft 134 which is fixedly mounted on the bearing plate 132. These levers include a downwardly extending portion, on the free end of which is mounted a sleeve 135 for engagement with the free end of the rod 131. These levers also include a horizontal portion, the free end of which is formed with a projection rotatably carrying rollers 136a, 136b. The guide tube 111 extends, in the axial direction thereof, through a sleeve 138 secured to a baseplate 137. Intermediate its length, the tube 111 is externally provided with a flange 139 which is secured thereto by means of set screws 139a, 139b. The rollers 136a, 136b are adapted to bear against the lower surface of the flange 139. A compression spring 140 is disposed between the flange 139 and the bottom plate 81A of the outer casing, thus normally urging the tube 111 in the downward direction. A sleeve 141 having a flange 141A of a greater diameter than the opening 110 formed in the bottom plate 85A is slidably fitted on the tube 111 above the flange 139. A compression spring 142 is disposed between the lower end of the sleeve 141 and the upper end of the flange 139 to maintain the upper surface of the flange 141A in abutment against the lower surface of the bottom plate 85A to provide a hermetically sealed connection between the interior of the inner casing 85 and the guide tube 111 when the closure 82 is closed as shown in FIG. 16. A circular lid 143 is mounted on a shaft 144 so as to be rotatable through nearly 90° on the top end of the guide tube 111. Specifically, the shaft 144 is pivotally mounted on a pair of ears 145a, 145b fixedly mounted on the outer wall of the tube 111, and pivotally carries a lug 146 which fixedly carries the lid 143. When the closure 82 is closed as shown in FIG. 16, the free end of the lug 146 bears against the edge of the opening 110 formed in the bottom plate 85A, whereby the lid 143 is maintained in its open position. However, when the closure 82 is opened, the lug 146 is disengaged from the edge of the opening 110 as the tube 111 moves down, so that the lid 143 rotates about the shaft 144 by its own gravity to hermetically seal the opening of the tube 111. In this manner, the tube 111 can be withdrawn in the downward direction until its top end is located below the bottom plate 85A of the inner casing, thus preventing its interference with a movement of the inner casing 85. As such, the tube 111 is moved into and out of the hole 110 in the bottom of inner casing 85 responsive to the closing and opening of closure 82, respectively.

It will be noted that if the opening 110 in the bottom plate 85A is left open when loading the inner casing 85 containing fresh centrifuge tubes 14 into the outer casing 81, miscellaneous strains may enter the interior thereof through this opening to cause the contamination of the centrifuge tubes. To avoid this likelihood, the bottom plate 85A of the inner casing is provided with a lid 147 (see FIG. 15) which is connected through an arm 148 with the shaft 149 so as to be rotatable thereabout to hermetically cover the opening 110. In the region adjacent to the shaft 149, a bearing 150 is fixedly mounted on the sidewall of the inner casing to slidably receive a rod 151 which is provided with an external and an internal stop 152a, 152b to limit its movement.

The inner end of the rod 151 is engageable with a lateral edge of the arm 148 which is connected with the lid 147 so that the latter covers the opening 110 before the inner casing 85 is inserted into the outer casing 81. Thus, the rod 151 assumes an outwardly projecting position at this time. However, when the inner casing 85 is inserted into the outer casing 81, the outer end of the rod 151 bears against the sidewall of the outer casing 81 to be forced inward. This movement of the rod 151 causes the arm 148 to rotate the lid 147 counterclockwise, as viewed in FIG. 15, thus opening the opening 110. In this manner, the ingress of miscellaneous strains into the inner casing 85 is positively prevented.

In the arrangement shown, there is provided a lock mechanism which prevents the rotation of the disc 101 before the inner casing 85 is placed inside the casing 81. Referring to FIG. 15, a bearing 153 is mounted on the sidewall of the inner casing 85 for rotatably receiving a lock bar 154. The lock bar 154 is generally channel-shaped, having an external portion 154A which projects externally of the casing 85 and an internal portion 154B which is folded in the manner of a crank shaft. A pin 155 is fixedly mounted on the upper surface of the rotary disc 101 at position 101A which is adjacent to the outer periphery thereof, and the pin is formed with a horizontally extending groove 155A in its top end which is engageable with the end of the internal portion 154B of the lock bar 154. Prior to the insertion of the inner casing 85 into the outer casing 81, the internal portion 154B can be fitted with the groove 155A to maintain the disc 101 at rest. However, when the casing 85 is inserted into the casing 81, the external portion 154A of the lock bar 154 bears against a horizontal pin 156 fixedly mounted on the inner sidewall of the outer casing 81 to be angularly driven, whereby the internal portion 154B is disengaged from the groove 155A to permit the rotation of the disc 101.

It will be understood that the inner casing 85 is located, upon insertion, by the pair of guide plates 93a, 93b (see FIG. 15) in a direction perpendicular to the direction of insertion. To provide a positioning of the casing 85 in the direction in which it is inserted, a pair of stops 157a, 157b (see FIG. 15) are mounted on a sidewall of the outer casing which opposes such direction, and a pair of stops 159a, 159b having internal coiled compression springs 158a, 158b associated therewith are mounted on the inner surface of the closure 82 as shown in FIG. 16. In this manner, the inner casing 85 is resiliently urged in the direction in which it is inserted until it assumes a given position within the outer casing 81, determined by abutment against the stops 157a, 157b when the closure 82 is closed.

Liquid disposal unit

The liquid disposal unit is disposed adjacent to the turntable 1 in alignment with the liquid disposal zone B (see FIG. 1) on the rotary plate 5 for causing the centrifuge tube holder mechanism to tilt a centrifuge tube located at this zone in order to dispose unnecessary supernatant liquid from the tube to the outside of the culturing environment. The liquid disposal unit 22 is associated with means 180 which prevents a free fall of the centrifuge tube (see FIG. 1).

Referring to FIG. 19, the liquid disposal unit 22 comprises a disposal vessel 161 having a large opening 161a formed in its top and having a drain hole 161b formed centrally in its bottom. In addition, the unit 22 includes a drain pipe (not shown) which is connected with the drain hole 161b for draining from within the vessel 161 to the outside of the culturing environment. The vessel 161 is fitted in an opening formed in the stationary plate 6, and is held in place by engaging its peripheral flange 161c with the edge of the opening. When tilted, the top opening of the centrifuge tube 14 is directed into the large opening 161a.

Figure 20:
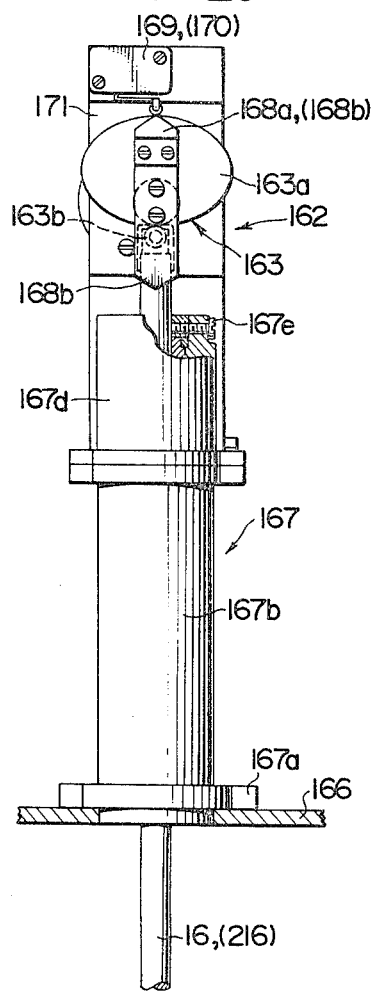
FIG. 20 is a front view of a drive mechanism for an elevating rod which causes a centrifuge tube holder to assume a tilted and an inverted position in the disposal and the discharge position, respectively.
Figure 21:
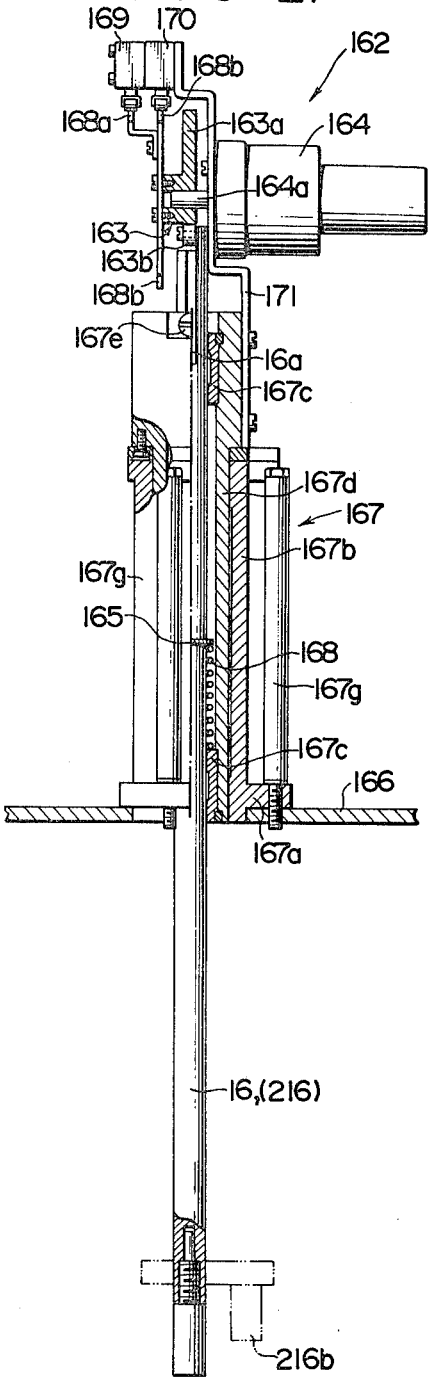
FIG. 21 is a side elevation of the drive mechanism shown in FIG. 20.

The centrifuge tube holder 13 located at the disposal zone B is tilted by the action of the centrifuge tube holder mechanism 15. FIGS. 20 and 21 show the elevating rod 16 and a drive mechanism 162 therefor which operate the holder mechanism 15. Specifically, the elevating rod 16 is driven in the downward direction by a cam assembly 163 mounted outside the culturing environment and a step motor 164 which drives the cam assembly 163. The rod 16 is driven in the upward direction by a return spring 168 located within a bearing member 167 which is mounted on a stationary plate 166. In the arrangement shown, the cam assembly 163 comprises an elliptical disc cam 163a fixedly mounted on the output shaft 164a of the motor 164, and a roller 163b mounted on the upper end of the rod 16 and urged into abutment against the cam 163a. A pair of microswitch actuators 168a, 168b are connected with the cam 163, and operate microswitches 169, 170 when they sense the lower and the upper position of the elevating rod 16, respectively. These microswitches are connected in circuit with a computer or other operating mechanism to enable related operations to be performed on the centrifuge tube 14. The step motor 164 is mounted on a bracket 171 which is secured to the bearing member 167, and is driven in response to a signal fed from a computer or the like.

The bearing member 167 includes an outer sleeve 167b having a bottom flange 167a which is clamped to the stationary plate 166 by means of an elongate bolt 167g, taking into consideration the spaced requirement for a heat insulating material. The member also includes an inner sleeve 167d which is fittingly fixed inside the outer sleeve 167b and having a bushing 167c for the elevating rod 16. A snap ring 165 is secured to the rod 16 intermediate its length, and a return spring 168 comprising a coiled compression spring is disposed between the ring 165 and another bushing 167c, thus normally urging the rod 16 in the upward direction. The purpose of forming the inner and the outer sleeve 167d, 167b as separate members is to facilitate the disassembly and reassembly of the rod 16 by allowing the rod 16 to be removed together with the inner sleeve 167d without requiring the disassembly of the outer sleeve which is surrounded by the heat insulating material whenever the elevating rod must be repaired. A locking pin 167e engages a longitudinal flute 16a formed in the upper portion of the rod 16 to guide the vertical movement of the rod 16.

Figure 22A:
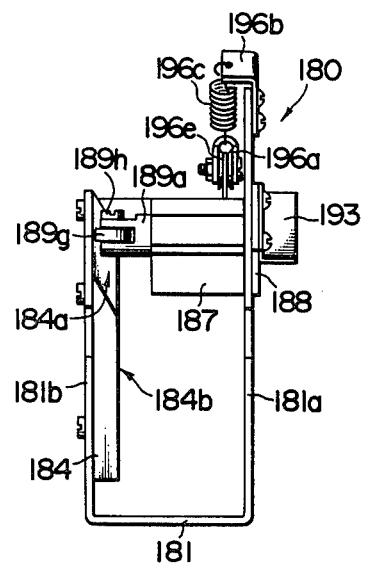
FIGS. 22A to D illustrate the various phases of means which prevent free fall of the centrifuge tube, FIG. 22A being a front view of such means, FIG. 22B a side elevation, FIG. 22C a side elevation showing one of the sidewalls and FIG. 22D a cross section of the means.

Means 180 for preventing a free fall of the centrifuge tube which is located adjacent to the disposal unit 22 is shown in detail in FIGS. 19 and 22A, B, C and D. As shown by enlarged views in FIG. 22, means 180 comprises a stationary wall 181 which is U-shaped in front elevation (see FIG. 22A) and having a pair of opposite sidewalls 181a, 181b which are secured to the stationary plate 6. An arcuate guide slot 183 (FIG. 22C) is formed in the sidewal 181a and a cam 184 is fixedly mounted on the other sidewall 181b generally in opposing relationship with the guide slot 183. Means 180 also comprises a shaft 189 which has its one end held resiliently in abutment against the cam surface 184 and having its other end extending through the guide slot 183 so as to be capable of axial movement under the control of the cam 184 and also capable of an angular movement along the slot 183 (see FIGS. 22C and D). Finally, means 180 comprises an abutment member 182 (see FIG. 22D) which is mounted on the outer end of the shaft 189 and which is adapted to bear against the outside of the centrifuge tube to prevent its withdrawal from the centrifuge tube when the shaft 189 projects axially outward.

The cam 184 is formed with an inclined surface 184a of a given width at its upper end, and also include a flat surface 184b of a constant elevation. An arcuate sliding piece 186 (FIGS. 22C and D) is disposed in the guide slot 183 for angular movement therein. A block 187 is secured to the inside and an operating plate 188 is secured to the outside of the sliding piece 186. In this manner, the plate 188 and the block 187 are supported by the sliding piece 186 on the opposite sides of the sidewall 181a so as to move angularly along the guide slot 183 together with the sliding piece 186. It is to be noted that the shaft 189 extends through the members 186, 187 and 188.

Figure 22B:
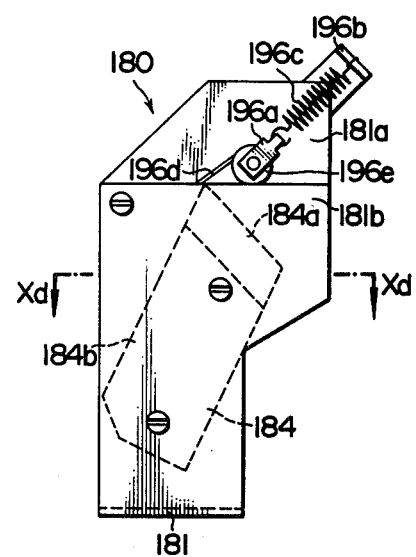
Figure 22C:
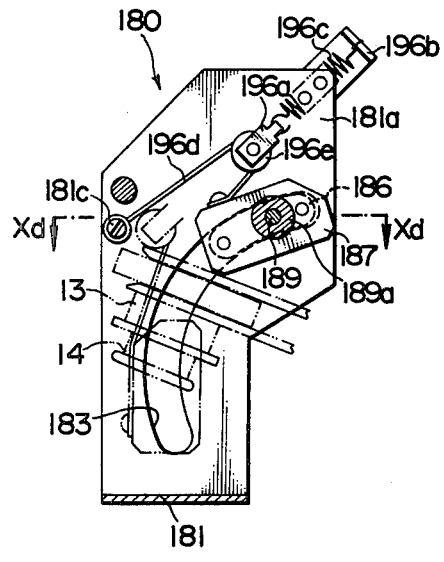
Figure 22D:
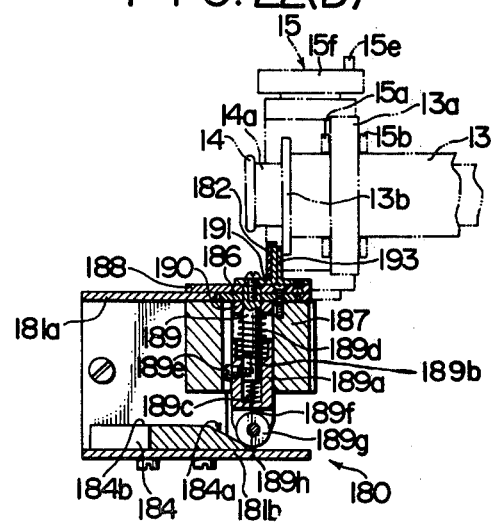

FIG. 22D is a cross section taken along the line Xd—Xd shown in FIGS. 22B and C. As shown, the shaft 189 is telescoped into the block 187. Specifically, a hollow shaft 189a of a reduced diameter is displaceably fitted inside the block 187, and receive part of the shaft 189. An axial relative movement between the hollow shaft and the shaft 189 is permitted by the engagement of the free end of a set screw 189e attached to the hollow shaft with a longitudinal groove 189b formed in the shaft 189. However, they are normally urged away from each other by a spring 189c disposed between a shelf 189f and the inner end of the shaft 189 and by another spring 189d disposed between the hollow shaft 189a and a spring abutment 190. The spring abutment 190 is fitted on the shaft 189 and is held in abutment against the inner surface of the sliding piece 186 under the resilience of the spring 189d. The inner end of the hollow shaft 189a projects from the block 187, and fixedly carries a pin 189h which rotatably carries a roller 189g for rolling engagement with the surface of the cam 184.

An L-shaped support 191 is fixedly mounted on the outer end of the shaft 189, and the abutment member 182 is in the form of an elastic material such as rubber, plastic or the like which is applied to the upright portion thereof. Another L-shaped detent piece 193 is disposed on the operating plate 188 adjacent to the support piece 191. The detent piece 193 is engageable with the flange 13b of the holder 13 to prevent its withdrawal from the holder mechanism 15 as it is angularly driven. The abutment member 182 is adapted to bear against the sidewall of the centrifuge tube 14 to prevent its withdrawal from the holder 13 when the centrifuge tube 14 is angularly driven to its tilted position.

A coiled compression spring 196c has its one end engaged with the bracket 196b which is on the top end of the sidewall 181a on the outside thereof, and has its other end fixedly connected with a pulley support 196a. The support 196a rotatably carries a pulley 196e, around which extends a length of wire 196d having its one end anchored to the block 187 and its other end connected with a pin 181c fixedly mounted on the sidewall 181a, whereby the return spring 196c is connected with the shaft 189.

The liquid disposal unit 22 and means 180 operate as follows. Assuming that a centrifuge tube 14 is located opposite to the unit 22 when the rotary plate 5 (see FIG. 1) stops, the drive mechanism 162 for the rod 16 is actuated. The motor 164 is set in motion to rotate the cam 163a, thus causing a downward movement of the rod 16 until it bears against the eccentric pin 15e on the disc 15f of the holder mechanism 15 (see FIG. 19). The continued rotation of the cam 163 causes the rod 16 to move further downward, causing the disc 15f to rotate together with its support shaft 15c. As a consequence, the holder 13 carrying the centrifuge tube 14 rotates together with the holder blades 15a, 15b until it is located opposite to means 180 associated with the liquid disposal unit 22.

As shown in phantom line in FIG. 22D, the detent piece 193 initially engages the flange 13b of the holder 13 holding the centrifuge tube 14 which has been already subjected to the centrifugation, and moves along the guide slot 183 which is concentric with the center of rotation of the holder 13 as the rod 16 continues to move downward. As a consequence, the shaft 189 also moves along the slot 183, whereby the roller 189g begins to roll on the inclined surface 184a of the cam 184. The rolling motion of the roller 189g retracts the hollow shaft 189a within the block 187 against the resilience of the springs 189c and 189d. On the other hand, the shaft 189, being guided by the sliding piece 186 and the operating plate 188, is driven out of the operating plate 188 under the resilience of the spring 189c. This brings the support 191 closer to the sidewall 14a of the centrifuge tube 14, and eventually the abutment member 182 is brought in abutment against the sidewall 14a to prevent its withdrawal from the holder 13 before the tube 14 begins to be withdrawn from the holder 13. It will be appreciated that a material for the abutment member 182 preferably has a large coefficient of friction to present a substantial frictional resistance to the movement of the centrifuge tube 14. It will also be appreciated that any slight variation in the outer diameter of the centrifuge tubes 14 can be satisfactorily compensated for by the resilience of the spring 189c which urges the shaft 189 out of the operating plate 188. It is to be noted that in order to complete the abutment of the member 182 against the centrifuge tube 14 before the latter begins to be withdrawn from the holder 13, the upper limit position of the guide slot 183 and the location of the cam 184 must be chosen such that the roller 189g has moved up the inclined surface 184a of the cam before the centrifuge tube 14 reaches its horizontal position.

As the holder 13 further rotates, the shaft 189 moves along the slot 183, so that the opening of the centrifuge tube 14 is directed downward as shown in FIG. 22C. Thereupon the supernatant liquid within the centrifuge tube 14 flows down into the vessel 161. Upon completion of this liquid disposal, or when the centrifuge tube 14 has rotated through the given angle, the drive mechanism 162 is actuated to cause an upward movement of the rod 16, and the shaft 189 is returned to its upper limit within the guide slot 183 under the resilience of the return spring 196c. During such returning movement, the abutment member 182 urges the centrifuge tube 14 until the roller 189g has moved past the flat surface 184b of the cam 184, whereupon it is urged by the spring 189d to move away from the side 14a of the centrifuge tube 14, together with the shaft 189. The centrifuge tube 14 is returned by a return spring, not shown, which is mounted within the holder mechanism 15. It should be noted that means 180 which is used to prevent a free fall of the centrifuge tube is not limited to the form illustrated. By way of example, a single shaft can be used to operate the abutment member 182. In addition, the abutment member 182 may be shaped into conformity with the outer profile of the centrifuge tube in order to increase the area of contact between the side 14a and the member 182.

CENTRIFUGE TUBE DISCHARGE UNIT

Centrifuge tube discharge unit 24 is located adjacent to the turntable 1 in alignment with discharge zone E (see FIG. 1) for causing a used centrifuge tube which is located at zone E to be inverted for external discharge from the holder subsequent to its rotation by the holder mechanism.

Referring to FIGS. 23 to 26, the discharge unit 24 comprises a funnel-shaped receiver 201 having an opening 201a. A discharge pipe 202 is connected with the lower end of the receiver 201, and the opening 201a may be closed by a lid member 204 which can be operated by a lever 207 which is pivotally mounted at 208 on the top end of the receiver 201 and having its one end connected with the lid member 204 and its other end located adjacent to a rod 216b. The bottom opening of the discharge pipe 202 is closed by a pair of resilient plates 211a, 211b having overlapping, mating edges. Receiver 201 is fixedly received in an opening in the stationary plate 6, and has the bottom opening 201b, around which the top of the discharge pipe 202 is fastened, the lower portion of the pipe 202 extending to the exterior of the culturing enviornment.

The lid member 204 is in the form of a rectangular plate which is pivotally mounted on a pair of brackets 203a, 203b (see FIG. 25) which are secured to the top periphery of the receiver 201 at diametrically opposite positions. At the juncture with the receiver 201, the brackets are soldered to the receiver and extend parallel to each other. The diameter along which the brackets are secured to the receiver is at right angles to the radius of the rotary plate 5, and these brackets extend in a direction away from the rotary plate 5.

Figure 23:
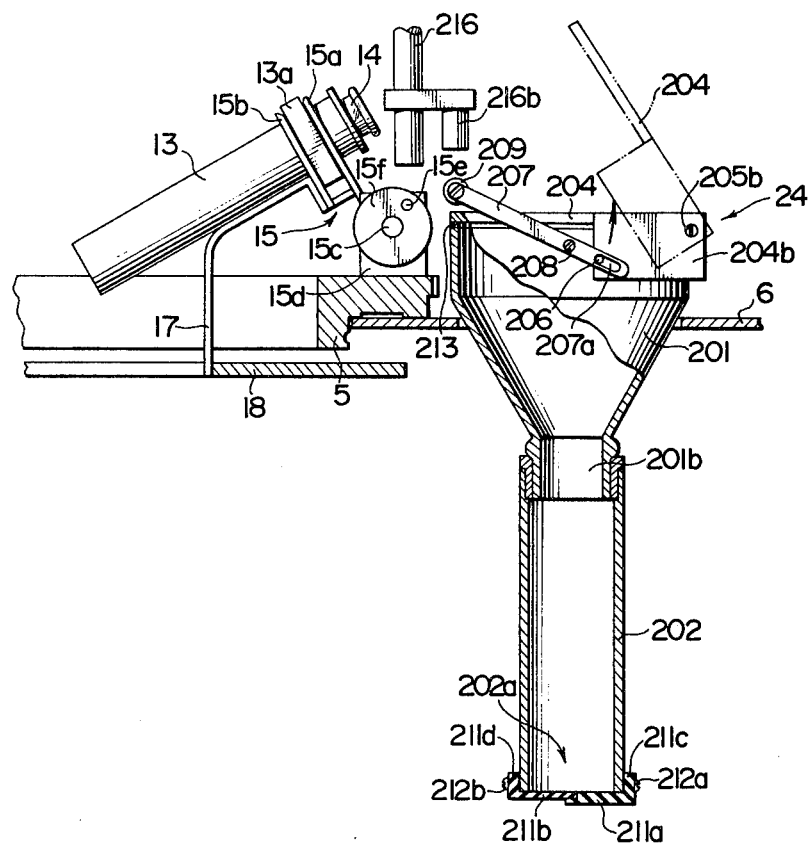
FIG. 23 is a side elevation, partly in section, of a centrifuge tube discharge unit.
Figure 24:
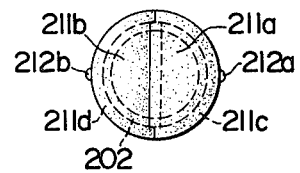
FIG. 24 is a bottom view of a discharge pipe used in the discharge unit of FIG. 23.
Figure 25:
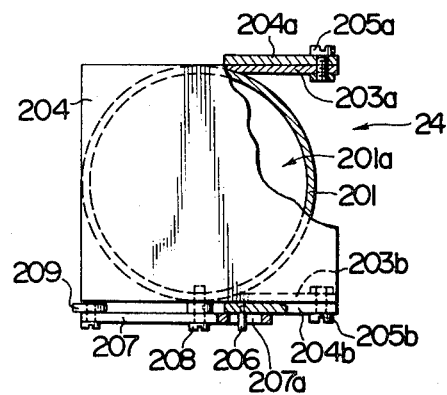
FIG. 25 is a plan view of the discharge unit shown in FIG. 23.

The lid member 204 is integrally provided with a pair of downwardly depending pieces 204a, 204b on its opposite sides in its outer region, or in the right-hand portion thereof as viewed in FIGS. 23 and 25, the depending pieces being disposed in overlying relationship with the brackets 203a, 203b. These pieces 204a, 204b are rotatably connected with the brackets 203a, 203b by means of screws 205a, 205b. As a consequence, the lid member 204 is rotatable about an axis defined by the screws 205a, 205b to its open position shown in phantom line in FIG. 23, thus opening the opening 201a. The pivot 208 is fixedly mounted on the top end of the receiver 201 adjacent to the depending piece 204b, and the lever 207 is pivotally mounted thereon. One arm of the lever 207 which extends along the outside of the depending piece 204b is formed with an elongate slot 207a, which is engaged by a pin 206 fixedly mounted on the depending piece 204b. In this manner, when the lid member is closed, the lever 207 assumes a position shown in FIG. 23 in which it is inclined downwardly toward the right. A roller 209 is mounted on the free end of the other arm of the lever 207 and is located opposite to the rod 216b, which represents an integral branch of the elevating rod 216 which is used to drive the eccentric pin 15e of the holder mechanism 15.

The elevating rod 216 and its drive mechanism are constructed in quite the similar manner as the elevating rod 16 and its associated drive mechanism 162 shown in FIGS. 20 and 21, and therefore will not be described in detail. However, the elevating rod 216 differs from the construction of the elevating rod 16 in that it is provided with lid operating rod 216b as an integral branch thereof. When the elevating rod 216 moves down, it drives the eccentric pin 15e on the holder mechanism 15 to cause a rotation of the support shaft 15c, turning the centrifuge tube holder 13 to its inverted position. Since the rod 216b drives the roller 209, the lever 207 is rocked clockwise about the pivot 208, thus opening the lid member 204.

As mentioned previously, the lower end of the discharge pipe 202 is normally closed by the pair of resilient plates 211a, 211b. These plates may be formed of an elastic material such as rubber disc, split into a pair of semicircular halves, with their rectilinear opposing edges disposed in overlapping relationship. At a location remote from the opposing edges, these plates have an upturned wall 211c, 211d which is secured to the sidewall of the pipe 102 as by set screws 212a, 212b. These resilient plates 211a, 211b function to absorb the kinetic energy of the centrifuge tube 14 as it falls, by pivoting about the respective fulcrums defined by the set screws in the manner shown in FIG. 26. It is desirable that the resilient plates comprise at least two members, and their thickness depends on the weight and the speed of falling movement of the centrifuge tube 14. As shown in FIG. 23, a seal member 213 is disposed on the top edge of the receiver 201 around the opening thereof.

The operation of the discharge unit 24 will now be described. When a used centrifuge tube 14 is located opposite to the receiver 201 at one of the stop positions of the rotary plate 5, the elevating rod 216 is driven downward by a drive motor, not shown. Thereupon, the free end of the rod 216 comes into abutment against the eccentric pin 15e, and the branch rod 216b abuts against the roller 209 on the lever 207. The continued downward movement of the elevating rod 216 causes the centrifuge tube holder 13 to rotate about the shaft 15c and to cause the lever 207 to rotate about the pivot 208. The counter-clockwise rotation of the lever 207 causes an upward movement of the pin 206 on the lid member 204 which engages the slot 207a therein, whereby the lid member 204 rotate clockwise about the screws 205a, 205b to its open position shown in phantom line in FIG. 23 to open the opening 201a.

In the meantime, the centrifuge tube 14 continues to rotate, and when the holder 13 reaches a horizontal position, it begins to be withdrawn from the holder 13. The used centrifuge tube is initially dropped into the funnel-shaped receiver 201, with its top opening directed downward, and is then guided by the sidewall of the receiver to be passed into the discharge pipe 202.

Figure 26:
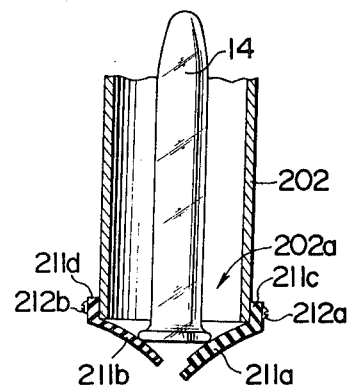
FIG. 26 is a fragmentary cross section of the discharge pipe, illustrating a centrifuge tube as it is being discharged.

When the centrifuge tube 14 has dropped into the discharge pipe 202, the rod 216 can be driven by a drive motor, not shown and a return spring to move upward to return the lid member 204 and the holder mechanism 15 to their respective original positions under the action of return springs or by gravity, thus closing the lid member 204. Subsequently, the centrifuge tube abuts against the resilient plates 211a, 211b, spreading them apart as shown in FIG. 26, and continue its free fall. In the process of collision with the resilient plates, part of the kinetic energy of the centrifuge tube is absorbed by these plates. The falling centrifuge tube can be received by an anti-shock container which is disposed outside the culturing environment at a position below the discharge pipe 202, thus completing the discharge process.

It is to be understood that the discharge unit employed need not be limited to the exact construction shown. By way of example, the resilient plates may comprise fan-shaped segments which overlap each other. The resilient plates may also be adhesively secured to the discharge pipe. The lid member may be formed in any desired configuration.

OPERATIONS

Various processing operations will now be described which take place as rotary plate 5 comes to a stop between the intermittent rotation of the turntable 1 through a given angular increment. In order to facilitate the understanding of the operation, it is assumed that four centrifuge tubes 14 containing injected tissues have been subjected to the centrifugation step in the centrifuge 2. In response to the interruption of the operation of the centrifuge 2, the step motor 34 of the drive mechanism 3 is actuated to move the positioning shaft 38 downward. This brings the end covers 30, 41h to their open position to permit the grippers 53c and the elevating shaft 54 of the conveyor mechanism 25 to pass therethrough. The free end of the pin 41 bears against the upper end face of rotatable arm 28a. The step motor 35 is then set in motion to engage the pin 40 with the depression 28d to determine the position of the rotor 28.

The holder mechanism 15 which is waiting on the turntable 1 receives the centrifuge tubes 14 from the conveyor drive mechanism 25. Simultaneously, the holder mechanism 15 located at zone A receives an empty centrifuge tube 14 from the delivery unit 21. The delivery unit 21 cooperate with the conveyor tube 112 (see FIG. 17) to drop a fresh centrifuge tube 14 into the holder 13.

When the both operations are completed, the drive motor 12, formed by a step motor, is set in rotation to rotate the turntable 1 through one eighth revolution. As a consequence, the initial zones A and F on the rotary plate 5 are brought into opposing relationship with the liquid disposal unit 22 and the centrifuge tube delivery unit 21, respectively. The centrifuge tube at the initial zone A has not yet received an injection of a culturing solution, and the initial zone F carries a centrifuge tube 14 from the centrifuge 2, so that neither unit operate at this position of the turntable 1. The initial zone G is brought into alignment with the conveyor mechanism 25, which however does not operate at such position.

The continued rotation of the turntable 1 through one eighth revolution brings the initial zones A and F into alignment with the culturing solution feeder supply unit 23 and the liquid disposal unit 22, respectively, and also brings the initial zones G and E into alignment with the centrifuge tube delivery unit 21 and the conveyor unit 25, respectively. The delivery and transfer of the centrifuge tubes take place at the zones G and E while the disposal of the supernatant liquid from the centrifuge tube subsequent to the centrifugation occurs at the initial zone F. Since the centrifuge tube 14 located at the initial zone A is still empty, no injection of the culturing solution takes place.

At this stop position of the turntable 1, when transferring the second centrifuge tube from the centrifuge 2 to the initial zone E, it is necessary to activate conveyor drive mechanism 25 in advance by supplying a signal from the microswitch 20 to the step motor 35 to cause a rotation of the rotor 28 through one fourth revolution at a time before the rotation of the turntable 1 through two eighth revolution is completed, for example, after rotation through one eighth revolution is completed. The same applies to the subsequent transfer of successive centrifuge tubes. By completing a rotation of the rotor 28 through one fourth revolution for each rotation of the turntable 1 through two eighth revolution, it is possible to maintain the designation of a particular centrifuge tube which is transferred back to the turntable 1 subsequent to the centrifugation.

The liquid disposal unit 22 which disposes the supernatant liquid comprises a centrifuge tube turning mechanism which causes the centrifuge tube to rotate about the shaft 15c by driving the pin 15e of the holder mechanism 15 in the same manner as the elevating rod 216 of the discharge unit 24. The unit 22 also comprises means 180 for preventing a free fall of the centrifuge tube 14 which undergoes an angular movement, while maintaining the engagement with the side of the centrifuge tube as it rotates in order to prevent a contamination of the tissues. Finally, the unit comprises the disposal vessel 161. Subsequent to the centrifugation, the tissues being cultured adhere to the bottom of the centrifuge tube 14 while deceased tissues and culturing solution are situated, in the form of the supernatant liquid, above the tissues which adhere to the bottom, and can be flown into the disposal vessel 161 as the centrifuge tube 14 is angularly driven by the mechanism described above. Thus, the tissues to be distributed remain within the centrifuge tube.

When the turntable 1 has completed three eighth revolution, the initial zone A will be brought into alignment with the culturing liquid supply and distribution unit, and the empty centrifuge tube 14 will be brought to its upright position there. A distributing device, not shown, is operated to distribute into the centrifuge tube the tissues being cultured which are withdrawn from a schale with a pipette while agitating them. The initial zone F will be opposed to the culturing solution supply unit 23, which injects a fresh culturing solution into the centrifuge tube 14 through a liquid switching device, not shown.

During such rotation of the turntable 1, the centrifuge tube 14 will be brought to its upright position when it is located opposite to the supply and distribution unit and the conveyor drive mechanism 25, while it is maintained in its inclined position at other stop positions as a result of the cooperation between the annular disc cam 18 and the follower arm 17, thus minimizing the likelihood that the tissues being cultured may be contaminated by miscellaneous strains or dust which falls freely.

When the turntable is further rotated through one eighth revolution to bring it to a position where it has completed one-half revolution, the initial zone F will be located opposite to the supply and distribution unit where a fresh culturing solution is injected into the centrifuge tube and the tissues being cultured is agitated by a pipette which is newly loaded for distribution. The agitation which occurs by using the pipette is accomplished by alternately withdrawing and discharging a given quantity of culturing solution from the centrifuge tube by pump means which is mounted within the distribution unit. As a consequence of such operation, the tissues adhering to the bottom of the centrifuge tube 14 will be made into a uniform suspension in the culturing solution. The distribution takes place by withdrawing the tissues in the tube with a pipette and splitting them into a pair of empty schales in equal amounts, which are located on a distribution table, not shown.

The initial zone E will be located opposite to the liquid disposal unit 22 while the initial zones H and D will be located opposite to the centrifuge tube delivery unit 21 and the conveyor mechanism 25, respectively, where operations as mentioned above take place.

A subsequent rotation of the turntable brings the initial zone G into alignment with the tissue supply unit where tissues contained in a schale is transferred into a centrifuge tube. In addition, the culturing solution supply unit 23 injects a culturing solution into a centrifuge tube which is located at the initial zone E.

The continued rotation of the turntable 1 through further one eighth revolution brings the initial zone F into alignment with the discharge unit 24 where the centrifuge tube 14 initially located at zone F is disposed. Simultaneously, the tissues being cultured in the centrifuge tube which has been located at the initial zone E will be distributed into a pair of empty schales. Also, the supernatant liquid is disposed by the disposal unit 22 from the centrifuge tube 14 which has been initially held at zone D. It will be also seen that the initial zones B and C are now supplied with empty centrifuge tubes 14, and the centrifuge 2 transfers the fourth centrifuge tube.

After completing the transfer of the centrifuge tube to the turntable 1, the centrifuge 2 is not indexed but remains in position until it receives the tissues being cultured which are to be subjected to the centrifugation after the further rotation of the turntable 1 through another one eighth revolution.

As mentioned previously, the discharge unit 24 comprises the elevating rod 216, branch rod 216b, receiver 201, lid member 204 of the receiver, and lever 207 which operates the lid member 204. The drive source for these members is energized in response to a signal from a microswitch or computer which is produced when the initial zone F reaches the position of the unit 24. Thereupon the rod 216 and the branch rod 216b move down integrally, driving the pin 15e and roller 209, respectively, to rotate the centrifuge tube 14 and to open the lid member 204 in the direction indicated by the arrow. The resulting rotation of the centrifuge tube 14 permits it to be withdrawn from the holder 13 to drop into the discharge pipe 202. After the discharge, the rods 216, 216b move upward to return the holder 13 and the lid member 204 to their original positions. The centrifuge tube 14 is discharged after each use and is replaced by a fresh one which is supplied by the delivery unit 21 in order to enable a pure culturing operation, by minimizing the chance of attachment and growth of miscellaneous strains to and on the tissues being cultured, through the use of fresh, sterilized centrifuge tubes.

After the rotation of the turntable through a futher one eighth revolution, the centrifuge tube 14 which was on the initial zone A will be conveyed to the rotor 28 within the centrifuge 2 while the empty centrifuge tube at the initial zone H will have an injection of the tissues being cultured from a schale. The centrifuge tube at the initial zone D will have an injection of the culturing solution. The centrifuge tube 14 is loaded into the centrifuge 2 by a procedure which is opposite to the transfer of the centrifuge tube from the centrifuge 2 to the holder mechanism 15 by means of the conveyor drive mechanism 25.

When the turntable 1 further rotates through one eighth revolution to complete one full revolution, the centrifuge tube located at the initial zone E will be discharged, the centrifuge tube at the initial zone D is used for distribution of the tissues subjected to the centrifugation, and the disposal of the supernatant liquid takes place from the centrifuge tube located at the initial zone B.

When the turntable 1 further rotates through one eighth revolution, the centrifuge tube located at the initial zone G will be loaded into the rotor 28 which is positioned as mentioned previously, and the centrifuge tube located at the initial zone C will have an injection of the tissues being cultured. The culturing solution is injected into the centrifuge tube located at the initial zone B.

Subsequently, when the turntable rotates through a further one eighth revolution, the centrifuge tube located at the initial zone D is discharged, and tissues contained in the centrifuge tube located at the initial zone B will be distributed into a pair of empty schales. Thereupon, the tissues which have been cultured in four schales prior to the centrifugation are now distributed into a total of eight schales for purpose of culturing while they are maintained at rest.

After the turntable 1 has rotated through eleven eighth revolutions, the third centrifuge tube located at the initial zone H will be loaded into the centrifuge. After twelve eighth revolutions, the centrifuge tube located at the initial zone B will be discharged. After thirteen eighth revolutions, the centrifuge tube at the initial zone C will be loaded into the centrifuge, whereupon the manipulation of the centrifuge tubes held on the turntable 1 is completed.

At this time, the rod 28 of the drive mechanism 3 moves upward to disengage the pin 40 from the depression 28d and closes the end covers 30, 41h in response to the detection of the status of operation of the conveyor mechanism 25 or a signal from the computer.

Subsequently, the turntable 1 is rotated until the microswitch 19 sensing the home position is actuated, whereupon it is brought to a stop. The centrifuge 2 is set in operation again in response to a signal from the microswitch 19 or from a computer.

The centrifugation may continue for a period of about ten minutes, and after the operation of centrifuge 2 is completed, the centrifuge tubes loaded in the centrifuge 2 may be replaced by other centrifuge tubes which contain fresh tissues being cultured.

From the foregoing description, it will be appreciated that the described disposition of the turntable 1 and the centrifuge 2 one above another permits an efficient transfer of the centrifuge tubes therebetween, thus achieving a substantial reduction in the waste time of the centrifuge.

What is claimed is:

1. Apparatus for handling centrifuge tubes in an automatic culture system, the apparatus comprising:
   a centrifuge;
   a turntable rotatably disposed vertically above said centrifuge and being adapted to be intermittently driven for rotation about the axis of a rotor drive shaft of said centrifuge through a given angular increment;
   a plurality of processing units, each located at respective predetermined positions where the rotation of the turntable is interrupted, said processing units including a selected combination of a transfer unit for transferring a centrifuge tube between the turntable and the centrifuge, a centrifuge tube delivery unit, a liquid disposal unit, a culturing solution supply unit, a tissue feed and distribution unit and a centrifuge tube discharge unit;
- a plurality of centrifuge tube holder mechanisms disposed on a common circumference of said turntable so as to be brought into alignment with the position of said respective units when the rotation of the turntable is interrupted; and
- a plurality of centrifuge tube holders detachably mounted in each of the holder mechanisms for detachably supporting a centrifuge tube.

2. Apparatus for handling centrifuge tubes in an automatic culture system, said apparatus comprising:
- a centrifuge;
- a turntable rotatably disposed vertically above said centrifuge and adapted to be rotated about the axis of a rotor drive shaft of said centrifuge;
- means for intermittently rotating said turntable about said axis through a given angular increment;
- a plurality of processing units including a transfer unit for transferring centrifuge tubes between said turntable and said centrifuge, a centrifuge tube delivery unit, a liquid disposal unit, a culturing solution supply unit, a tissue feed and distribution unit and a centrifuge tube discharge unit;
- a plurality of centrifuge tube holder mechanisms disposed on a common circumference of said turntable such that each said centrifuge tube holder is brought into alignment with each of said units as said turntable is intermittently rotated; and
- a plurality of centrifuge tube holders, each of said tube holders being detachably mounted in a respective one of said holder mechanisms and being adapted to detachably support a respective centrifuge tube.

3. Apparatus according to claim 1 in which the turntable comprises a rotary plate having a central opening, a drive motor connected with the rotary plate for driving it for rotation, a cam follower arm connected with each of the holder mechanisms on the rotary plate for tilting a centrifuge tube, and an annular cam fixedly disposed below the rotary plate for cooperating with the cam follower arm to cause a centrifuge tube to assume a tilted and an upright position at given angular positions of the rotary plate.

4. Apparatus according to claim 3 in which the rotary plate is annular in configuration and is peripherally formed with a gear which serves to drive it for rotation.

5. Apparatus according to claim 3 in which the cam follower arm comprises a folded plate having its one end connected with each of the holder mechanisms and having its free end held in abutment against the cam profile of the annular cam.

6. Apparatus according to claim 3 in which the annular cam has an opening, the edge of which defines a cam profile, and is provided with a pair of recesses in the cam profile which cause a centrifuge tube to assume its upright position.

7. Apparatus according to claim 1 or 2 in which the transfer unit comprises an elevating shaft extending through the central opening in the turntable and carrying a holder support member which extends toward the rotor of the centrifuge, a carrier arm secured to the support member and having grippers which are detachably engageable with a centrifuge tube holder, a rotary drive mechanism associated with the elevating shaft for angularly displacing the grippers of the carrier arm between a first position over the turntable where they are capable of inserting or removing a centrifuge tube therefrom and a second position directly above the rotor, and a vertical drive mechanism associated with the elevating shaft for vertically displacing the grippers between the second position and a third position where the centrifuge tube can be transferred to or from the rotor.

8. Apparatus according to claim 7 in which the rotary drive mechanism comprises a pipe fitted over the elevating shaft for integral rotation, a disc integrally mounted on the pipe, and reversible drive motor for angularly driving the disc through a given angle.

9. Apparatus according to claim 7 in which the vertical drive mechanism comprises a rack mounted on the elevating shaft for integral movement in the axial direction thereof, a pinion meshing with the rack, and a reversible motor for rotating the pinion.

10. Apparatus according to claim 7, further including a rotor positioning device which is capable of bringing the rotor to and maintaining it at rest at the third position.

11. Apparatus according to claim 10 in which the rotor positioning device comprises a positioning shaft disposed above the rotor drive shaft and extending through the central opening in the turntable, the positioning shaft being rotatable and vertically movable with respect to the rotor drive shaft, a positioning pin secured to the lower end of the positioning shaft at a given eccentricity, and a depression formed in the top surface of the rotor and adapted to be engaged by the positioning pin.

12. Apparatus according to claim 11 in which the depression is formed by a groove which extends radially from the rotor drive shaft.

13. Apparatus according to claim 11 in which the positioning pin is mounted on the positioning shaft in a manner to be movable relative thereto and normally urged downward by a spring.

14. Apparatus according to claim 11 in which the positioning shaft carries a mechanism for opening and closing an end cover of the centrifuge.

15. Apparatus according to claim 14 in which the mechanism for opening and closing the end cover comprises a sleeve rotatably fitted over the positioning shaft, a roller secured to the sleeve and projecting radially outward thereof, a cylindrical, stationary guide member through which the positioning shaft extends and being formed with a skewed slot which permits the roller to extend therethrough, a cylindrical member formed with a longitudinal groove engaged by the roller and having an outer periphery to which the end cover is attached, and a fixed cam member for moving the cylindrical member in the vertical direction.

16. Apparatus according to claims 1 or 2 in which the centrifuge tube delivery unit comprises an outer casing having a closure which can be opened and closed, an inner casing which can be inserted into or removed from the outer casing through the closure, a spiral guide wall formed within the inner casing to define a spiral guideway, a rotary disc disposed above the guide wall so as to be rotatable about the center of the spiral guideway and being formed with a number of radially extending delivery slots which cooperate with the spiral guide wall to define a number of compartments, each of which is capable of receiving one centrifuge tube, and a guide tube spaced from one end of said spiral guideway for guiding a centrifuge tube leaving said guideway toward one of said plurality of centrifuge tube holders.

17. Apparatus according to claim 14 in which the closure is located on one side of the outer casing, and in which the inner casing can be inserted into the outer casing along the bottom of the outer casing when the closure is open.

18. Apparatus according to claim 16 in which a rotary drive mechanism associated with the rotary disc includes a part which is located within the inner casing and to which a rotary drive is transmitted through an opening formed in the bottom of the inner casing, a rotary drive transmission which supplies said rotary drive mechanism part, said rotary drive transmission being movable between a first position out of the inner casing wherein said transmission is out of contact with said rotary drive mechanism part and a second position in said inner casing wherein said transmission is in contact with said rotary drive mechanism part.

19. Apparatus according to claim 18 in which the rotary drive transmission is moved into said first position when said closure is opened and is moved into said second position when said closure is closed.

20. Apparatus according to claim 16 in which the guide tube is movable into and out of the inner casing through an opening formed in the bottom of the inner casing.

21. Apparatus according to claim 20 in which the guide tube is moved into and out of the inner casing responsive to the closing and opening, respectively, of the closure of the outer casing.

22. Apparatus according to claim 20 in which said guide tube has a lid formed on the top opening thereof, said lid being movable between an open and a closed position, said lid adapted to move into said open position responsive to the movement of said guide tube into said inner casing and adapted to move into said closed position responsive to the movement of said guide tube out of said inner casing.

23. Apparatus according to claim 1 or 2 in which the centrifuge tube holder comprises a cylinder having an opening formed in its top for receiving a centrifuge tube and closed at its bottom, a flange formed around the periphery of the top opening of the cylinder, another flange formed around the outer periphery of the cylinder at a position below the first mentioned flange, a pair of flutes formed in the lower surface of said another flange and adapted to engage a holder receiver that is provided on the part of the rotor of the centrifuge, and a cushioning elastic member applied to the inner surface of the sidewall and the bottom wall of the cylinder.

24. Apparatus according to claim 1 or 2 in which the centrifuge tube holder mechanism comprises a pair of holder blades having a semi-circular notch formed in the free end thereof for abutment against the outer peripheral surface of the centrifuge holder, the pair of holder blades being adapted to hold a flange of the centrifuge holder, a shaft rotatably mounted in a horizontal position on the turntable for supporting the opposite end of the holder blades, a rotary disc fixedly mounted on the shaft and having an eccentric pin which serves driving the shaft for rotation.

25. Apparatus according to claim 24 in which the eccentric pin is adapted to be driven by an elevating rod to rotate the shaft about its own axis at one position where a liquid is to be disposed from a centrifuge tube and another position where a centrifuge tube is to be discharged.

26. Apparatus according to claim 25 in which the elevating rod is driven in a first direction by a cam which is rotated by a motor, and is driven in a second direction by a return spring disposed on the rod.

27. Apparatus according to claim 1 or 2 in which the centrifuge tube discharge unit comprises a funnel-shaped vessel having an opening which receives a centrifuge tube, a discharge pipe connected with the lower end of the vessel, a lid member disposed to open or close the top opening of the vessel, a lever pivotally mounted on the outer periphery of the vessel and having its one end engaged with the lid member and its other end located adjacent to a lid member operating rod, and a pair of resilient plates attached to the lower end of the discharge pipe and having their free end disposed in superimposed relationship so as to close the bottom opening of the pipe.

28. Apparatus according to claim 27 in which the lid member operating rod is integral with an elevating rod which drives an eccentric pin of the centrifuge tube holder mechanism.

29. Apparatus according to claim 27 in which the pair of resilient plates are semi-circular in configuration, with their rectilinear edges disposed in overlapping relationship, the resilient plates being yieldable by a centrifuge tube which falls down from the vessel through the discharge pipe, thereby discharging the centrifuge tube to the outside thereof.

30. Apparatus according to claim 1 or 2 in which the liquid disposal unit comprises a disposal vessel having a top opening of a greater diameter and a liquid drain hole in its bottom, and means disposed adjacent to the disposal vessel for preventing a free fall of a centrifuge tube therefrom.

31. Apparatus according to claim 30 in which said means for preventing a free fall of the centrifuge tube comprises a pair of oppositely located sidewalls, an arcuate guide slot formed in one of the sidewalls, a cam fixedly mounted on the inside of the other sidewall in opposing relationship with the guide slot and having an inclined cam surface, a shaft having its one end extending through the guide slot and its other end resiliently held in abutment against the inclined cam surface and capable of axial movement under the control of the cam and of an angular movement along the guide slot, an abutment member attached to said one end of the shaft externally of said one sidewall and adapted to be brought into abutment against the outer surface of a centrifuge tube to prevent its withdrawal from the centrifuge tube as the shaft moves axially outward, and a return spring for the shaft.

32. Apparatus according to claim 31 in which the abutment member comprises a resilient material.

* * * * *